United States Patent [19]

Allen

[11] 4,451,571

[45] May 29, 1984

[54] PREPARATION OF SAMPLES FOR VITAMIN B12 AND/OR FOLATE ASSAY AND ASSAY

[75] Inventor: Robert H. Allen, Englewood, Colo.

[73] Assignee: University Patents, Inc., Norwalk, Conn.

[21] Appl. No.: 251,249

[22] Filed: Apr. 6, 1981

[51] Int. Cl.³ ............... G01N 33/56; G01N 33/82; G01N 1/00
[52] U.S. Cl. ............... 436/505; 436/825; 436/826; 436/527; 436/8; 436/175
[58] Field of Search ............... 424/1, 1.5; 23/230 B; 436/505, 8, 174, 175, 825, 826, 527

[56] References Cited

U.S. PATENT DOCUMENTS

| | | | |
|---|---|---|---|
| 3,981,863 | 9/1976 | Niswender et al. | 436/825 |
| 4,146,602 | 3/1979 | Gutcho et al. | 424/1 |
| 4,166,103 | 8/1979 | Wagner et al. | 424/1 |
| 4,166,104 | 8/1979 | Wagner et al. | 424/1 |
| 4,188,189 | 2/1980 | Allen | 424/1 |
| 4,225,784 | 9/1980 | Barrett | 250/303 |
| 4,271,140 | 6/1981 | Bunting | 424/1 |
| 4,279,859 | 7/1981 | Gutcho et al. | 422/61 |
| 4,300,907 | 11/1981 | Mansbach et al. | 23/230 B |
| 4,332,786 | 6/1982 | Cabelli et al. | 424/1 |
| 4,333,918 | 6/1982 | Carney et al. | 424/1 |
| 4,351,822 | 9/1982 | Allen | 424/1 |
| 4,355,018 | 10/1982 | Hansen et al. | 424/1 |

OTHER PUBLICATIONS

Zucker, R. M. et al., Ligand Quarterly, vol. 4, No. 3, pp. 52–58 (1981), Note Comments and Reply, pp. 59–63.
Allen, R. H., Ligand Quarterly, vol. 4, No. 3, pp. 37–44, 67, (1981).
Clinical Chemistry, vol. 26, No. 5, pp. 598–600, Apr. 1980, Kubasik et al.
New England Journal of Medicine, vol. 299, No. 15, pp. 785–792, 716–718, Kolhouse et al., Cooper et al., Oct. 1978.
Proceedings of the National Academy of Sciences, U.S.A., vol. 77, No. 2, pp. 817–821, Feb. 1980, Kondo et al.

*Primary Examiner*—Benjamin R. Padgett
*Assistant Examiner*—M. Moskowitz
*Attorney, Agent, or Firm*—George M. Yahwak

[57] ABSTRACT

Vitamin $B_{12}$ (cobalamin) and/or folate (folic acid) assay techniques can be simplified, by eliminating the step of heating or boiling the to-be-tested sample prior to its assay. This is accomplished by utilizing compositions and procedures:

(1) which substantially completely liberate all vitamin $B_{12}$ and/or folate from endogenous binding protein without heating or boiling;

(2) which substantially completely destroy all endogenous binding protein which is present in the to-be-assayed sample, and which may bind natural and radioactive vitamin $B_{12}$ or folate both due to its liberation from vitamin $B_{12}$ or folate in the original sample or due to its unbound presence in the original sample;

(3) which substantially completely inhibit or block any undestroyed endogenous binding protein; and (4) which substantially completely inhibit or destroy any intrinsic factor-blocking antibodies which may be present in the to-be-assayed sample.

In preferred embodiments the protein destroying compositions utilized include both a strong base and a sulfhydral compound which is a strong disulfide protein destroying material while the material of choice to bind with undestroyed endogenous binding protein is a vitamin $B_{12}$ analogue.

The sample is then assayed using known, for example, radioisotrope dilution assay techniques.

23 Claims, No Drawings

PREPARATION OF SAMPLES FOR VITAMIN B12 AND/OR FOLATE ASSAY AND ASSAY

BACKGROUND OF THE INVENTION

1. Field of the Invention

The present invention relates to methods and materials for preparing mammalian blood and tissue for assay, and to the resulting assay. More specifically it relates to methods and materials for preparing human serum for assay of vitamin $B_{12}$ (cobalamin) and/or folate (folic acid).

2. Prior Art

For many years it has been recognized that the assay of the vitamin $B_{12}$ in humans is a valuable technique for diagnosing and subsequently treating certain diseases which cause a deficiency of vitamin $B_{12}$, such as for example, pernicious anemia, post gastrectomy states, nutritional deficiencies, intestinal disorders, and/or other conditions where the blood level of vitamin $B_{12}$ is frequently depressed. The assay of vitamin $B_{12}$ in humans has also been useful for diagnosing certain myeloproliferative diseases, such as chronic myelogenous leukemia where the blood level of vitamin $B_{12}$ is frequently elevated. Initially vitamin $B_{12}$ was assayed for example, using either *Euglena gracilis* or *Lactobacillus leichmannii* in microbiologic assays. More recently, radioisotope dilution (RID) assays for vitamin $B_{12}$ have been utilized. Such radioisotope dilution assay techniques for vitamin $B_{12}$ are well documented in the literature, see for example Lau, et al. (1965) "Measurement of Serum $B_{12}$ Levels Using Radioisotope Dilution and Coated Charcoal," BLOOD, 26, 202, as modified by Raven et. al. (1968) "The Effect of Cyanide Serum and Other Factors on the Assay of Vitamin $B_{12}$ by Radio-Isotope Method Using $^{57}Co$-$B_{12}$, Intrinsic Factor and Coated Charcoal," GUYS HOSPITAL REPORTS, 117, 89; and (1969) "Improved Method for Measuring Vitamin $B_{12}$ in Serum Using Intrinsic Factor, $^{57}Co$-$B_{12}$ and Coated Charcoal," JOURNAL OF CLINICAL PATHOLOGY, 22, 205. More recently the presence of vitamin $B_{12}$ analogues in samples has been found, which analogues falsely contribute to the apparent vitamin $B_{12}$ level found by radioisotope dilution assay, unless the binding protein utilized in the assay is specific to vitamin $B_{12}$, as for example, either pure intrinsic factor, or binding protein which has been treated to eliminate or inactivate binding proteins which are non-specific to vitamin $B_{12}$, see Allen U.S. Pat. No. 4,188,189, Allen U.S. application Ser. No. 069,257, filed Aug. 24, 1979, and Kolhouse, et. al. (1978) "Cobalamin analogues are present in human serum and can mask Cobalamin deficiency . . . " N. ENG. J. MED. 229, 784.

In view of these prior art developments, current radioisotope dilution assay of vitamin $B_{12}$ generally includes the steps of freeing the endogenous vitamin $B_{12}$ from its endogenous natural binding protein by, for example, heating or boiling to-be-tested serum samples according to the teaching of Kolhouse et. al., adding an amount of intrinsic factor binding protein from which non-specific binding protein has been eliminated or inactivated, and radioactive vitamin $B_{12}$, for example $^{57}Co$-$B_{12}$, in a known amount which is adequate by itself to bind all of the intrinsic factor. Thus, all of the added intrinsic factor binding protein should be bound, either by the vitamin $B_{12}$ present from in the sample undergoing test, or by the radioactive vitamin $B_{12}$ added to the composition. As both the natural vitamin $B_{12}$ and the radioactive vitamin $B_{12}$ compete dynamically in the reaction to bind with the limited amount of intrinsic factor binding protein, the degree to which the radioactive count of the intrinsic factor protein bound-vitamin $B_{12}$ is inhibited or reduced is indicative of the amount of natural vitamin $B_{12}$ which is present in the sample undergoing testing. The inhibition of the binding of the radioactive vitamin $B_{12}$ with intrinsic factor is determined, both natural and radioactive, for example, by separating all unbound vitamin $B_{12}$ from the intrinsic factor protein bound vitamin $B_{12}$ by, for example, using protein-coated charcoal which adsorbs the unbound radioactive vitamin $B_{12}$. Then the radioactivity of the supernatant liquid containing the mixture of intrinsic factor bound radioactive vitamin $B_{12}$ and intrinsic factor bound non-radioactive vitamin $B_{12}$ is counted for radioactivity. The vitamin $B_{12}$ concentration in the sample undergoing testing is then determined from the count, often by comparison with a standard chart using techniques well known in the art.

Folate RID analysis is quite similar, although it uses radioactive folate and a folate binder for the same purpose.

As already noted, it has recently been recognized by Kolhouse et. al. that vitamin $B_{12}$ measurements previously provided were often inconsistent with the results obtained by other measuring techniques for vitamin $B_{12}$, such as the microbiological assays. Most often, the vitamin $B_{12}$ assay obtained by radioisotope dilution assay techniques had been found to be high. The determination by Kolhouse et. al. that there are vitamin $B_{12}$ analogue substances in mammalian blood and tissue which react with the non-specific protein binders which were then in use in prior art RID assay techniques explained why many prior art analyses of vitamin $B_{12}$ tested higher than the amount of vitamin $B_{12}$ actually in the sample. After the determination by Kolhouse et. al. that portions of most prior art binding protein included substantial amounts of binding protein which was not specific to vitamin $B_{12}$ and which was capable of binding with vitamin $B_{12}$ analogues; the corrective techniques were developed by Allen. As a result of Allen's work, current RID assays now use only pure or purified intrinsic factor binding protein, from which non-specific binding protein has been removed or inactivated, so that it is specific in its binding reaction only with vitamin $B_{12}$, and can not bind with vitamin $B_{12}$ analogues.

Folate RID analysis is far less demanding as there are no similar problems with folate analogues and no similar problems with non-specific folate binder, however, even improved specific vitamin $B_{12}$ RID assay techniques, using only intrinsic factor as the binding protein and the folate assay, still require the heating (or boiling) of samples prior to testing, in order to liberate vitamin $B_{12}$ and/or folate in the to-be-tested sample from endogenous binding protein. The current heating step is difficult to control, tedious and time consuming in terms of handling, capping and uncapping test tubes, and does not allow a process in which samples can be tested without heating.

Recently, means of denaturing samples chemically, to liberate vitamin $B_{12}$ from endogenous binding protein without boiling, have been reported. Ithakissios et. al. (1980) "Room Temperature Radioassay for $B_{12}$ with Oyster Toadfish (Opsanus tau) serum as binder", CLINICAL CHEMISTRY, 26, 323 has reported that the use of NaOH at pH 13.6 in the presence of KCN provided more than 98% release of vitamin $B_{12}$, with the release increasing to 100% when Ficol was used to replace human serum albumin. It also discussed vitamin $B_{12}$ release results for vitamin $B_{12}$ from protein at pH environments in the range of 2-12. Ithakissios et. al. did not discuss the effect of released endogenous binding protein in the to-be-assayed sample, or recognize any potential problem which might be caused by the presence of abnormally high amounts of endogenous binding protein or intrinsic factor-blocking antibodies which may be naturally present in some samples. A label for a commercial kit, dated October 1980, from RIA Products, Inc., Waltham, Mass "No-Boil Combostat T.M. Kit for simultaneous radioassay of FOLATE and VITAMIN $B_{12}$" has recently been noted as disclosing the use of NaOH as a denaturing agent in the presence of 0.01% KCN and dithiothreitol in a no-boil technique for analyzing both folate and vitamin $B_{12}$. It also does not discuss the effects of undestroyed endogenous binding protein on the vitamin $B_{12}$ assay or recognize any potential problem caused by the presence of high amounts of endogenous binding protein or intrinsic factor-blocking antibodies in some samples.

In a similar manner an undated label for a commercial kit, from Diagnostic Products Corporation, Los Angeles, Calif., "No-Boil Dualcount", radioassay for vitamin $B_{12}$ and folic acid, has also been noted as disclosing the use of NaOH, KCN and dithiothreitol in another no-boil technique for analyzing both folate and vitamin $B_{12}$. Again, this technique does not discuss or recognize the potential for any problem in the vitamin $B_{12}$ assay due to undestroyed endogenous binding protein or the presence of intrinsic factor-blocking antibodies or high amounts of endogenous binding protein.

In each of these prior art techniques KCN is normally added for the primary purpose of converting the vitamin $B_{12}$ in the sample to its most stable form, cyanocobalamin. Similarly, dithiotreitol is normally used in folate assays, and therefore in dual vitamin $B_{12}$-folate assays, as a means of stabilizing folate during the folate assay.

Currently, the best documented RID vitamin $B_{12}$-folate dual assay technique became available in December 1980 from Corning, Medfield, Mass. "Vitamin $B_{12}$ [$^{57}$Co]/Folate [125I] Radioassay" Immophase,$_{TM}$ (For the simultaneous determination of vitamin $B_{12}$, and folate in serum, plasma and red blood cells.) The documentation and accuracy of this kit and test are greater than for any known prior-art kit.

BRIEF DESCRIPTION OF THE INVENTION

As has already been indicated, in most standard prior art radioisotope dilution assays for vitamin $B_{12}$ and/or folate, the to-be-assayed sample is heated or boiled, to separate the sample vitamin $B_{12}$ and/or folate from endogenous binding protein. In more recent techniques the separation has been obtained without boiling by using a strong base with or without other chemicals. Then a known amount of radioactive vitamin $B_{12}$ and/or radioactive folate is mixed with a prepared to-be-tested sample and a known amount of specific binding protein which is capable of binding with both the natural and radioactive vitamin $B_{12}$, (but incapable of reacting with vitamin $B_{12}$ analogues) and/or folate binder is added to the mixture. Subsequently, utilizing well-known techniques, the radioactivity of the bound sample is compared, for example, with a standard curve to determine the amount of natural vitamin $B_{12}$ or folate present in the sample undergoing assay.

It has now been discovered that, in accordance with the teaching of the present invention, the RID assay techniques can be simplified, improved and in many instances, rendered more accurate by eliminating the step of heating or boiling the to-be-tested sample prior to its assay. This is accomplished by utilizing compositions and procedures:

(1) which substantially completely liberate all vitamin $B_{12}$ and/or folate from endogenous binding protein without heating or boiling:

(2) which substantially completely destroy all endogenous binding protein which is present in the to-be-assayed sample, and which may bind natural and radioactive vitamin $B_{12}$ or folate both due to its liberation from vitamin $B_{12}$ or folate in the original sample or due to its unbound presence in the original sample;

(3) which substantially completely inhibit or block any undestroyed endogenous binding protein; and (4) which substantially completely inhibit or destroy any intrinsic factor-blocking antibodies which may be present in the to-be-assayed sample.

Failure to consider and carry out these procedures in a no-boil test may result in erroneous vitamin $B_{12}$ and/or folate RID assay, as documented and detailed below.

This is accomplished by treating vitamin $B_{12}$ and/or folate samples which are to-be-assayed without heating or boiling, with compositions and procedures which substantially completely liberate vitamin $B_{12}$ and/or folate from endogenous binding protein, without heating or boiling; which substantially completely destroy substantially all endogenous binding protein present in the sample, whether liberated from vitamin $B_{12}$ and/or folate or otherwise present in the sample; which substantially inhibit or block undestroyed endogenous binding protein which has not been destroyed; and which inhibits or destroys substantially all intrinsic factor-blocking antibodies which are present in the to-be-assayed sample. More specifically, combinations of ingredients and procedures are taught which provide the foregoing results.

As has already been noted, a number of techniques are now publicly known and available which indicate that they release, without heating or boiling, vitamin $B_{12}$ and folate from a to-be-assayed sample. However, the present invention is based on the recognition of facts, apparently not known, or not understood, or ignored by other RID no-heat methods:

(1) that optimum release of vitamin $B_{12}$ and/or folate from a to-be-assayed sample must be achieved to obtain accurate vitamin $B_{12}$ measurement;

(2) that while boiling apparently substantially destroys endogenous binding protein, whether released from vitamin $B_{12}$ or otherwise present in the to-be-assayed sample, that currently published no-heat methods allow substantial amounts of endogenous protein to survive in some blood samples which may result in inaccurate assays of vitamin $B_{12}$ in these samples, as detailed below; and (3) that there are antibodies naturally present in some samples which antibodies react with or block intrinsic factor protein used for current state-of-the-art vitamin $B_{12}$ RID assays, in accordance with the teaching of Kolhouse et al and Allen, which antibodies may also result in inaccurate assays of vitamin $B_{12}$, as also detailed below.

In the absence of the recognition of these problems and the use of the procedures and compositions of the present invention to deal with them, seriously inaccurate vitamin $B_{12}$ assays will be obtained for a clinically unacceptable number of vitamin $B_{12}$ abnormal patients using current no-boil techniques and certain of the Kolhouse et. al and Allen RID assay procedures, even though the Kolhouse et. al. and Allen procedures provide the greatest accuracy for boiling techniques. For example, undestroyed or uninhibited endogenous binding protein present in a sample after no-boil release is available during the assay incubation period to react with both sample and radioactive vitamin $B_{12}$. This may result in a false, either high or low vitamin $B_{12}$ reading, depending on the technique which is used to separate bound and unbound vitamin $B_{12}$.

In another instance, where antibodies capable of binding with intrinsic factor are present in the sample, but have not been destroyed by boiling, in the Kolhouse et. al. and Allen RID assay procedures using intrinsic factor as the binding protein, the intrinsic factor which is added and expected to only react with and bind with sample and radioactive vitamin $B_{12}$ may react with intrinsic factor blocking antibodies, therefore making some intrinsic factor unavailable to react with radioactive and sample vitamin $B_{12}$. This reaction of intrinsic factor thus results in a lower amount of both types of vitamin $B_{12}$ being bound with intrinsic factor, due to the added competition for the intrinsic factor from the antibody, which in turn will be seen as a lower bound radioactive vitamin $B_{12}$-intrinsic factor concentration, and be analyzed, in the absence of the teaching of the present invention, as a higher amount of vitamin $B_{12}$ in the assayed sample.

It is also clearly apparent, without the need for detailed explanation, that failure to release substantially all vitamin $B_{12}$ or folate from endogenous binding protein in a to-be-assayed sample will result in an erroneous low vitamin $B_{12}$ or folate reading.

Finally, it has recently been noted that some subjects with abnormally high amounts of both vitamin $B_{12}$ and endogenous binding protein in their blood serum, such as subjects with chronic myelogenous leukemia, may be assayed at lower vitamin $B_{12}$ levels than actually exist, due to the competition of the excess endogenous binding protein for radioactive vitamin $B_{12}$, as explained above in the discussion of uninhibited endogenous binding protein in a sample after no-boil release.

Based on these discoveries, it is now proposed that samples being prepared for vitamin $B_{12}$ and/or folate assay be treated with compositions which liberate vitamin $B_{12}$ from endogenous protein, substantially destroy endogenous binding protein and intrinsic factor (IF) blocking antibodies, and which react with or inhibit any undestroyed endogenous binding protein, rendering it unavailable to bind with any form of vitamin $B_{12}$. In preferred embodiments the protein destroying compositions utilized include both a strong base and a sulfhydral compound which is a strong disulfide protein destroying material while the material of choice to bind with undestroyed endogenous binding protein is a vitamin $B_{12}$ analogue. Based on these discoveries, it is also now proposed that large numbers of samples from low vitamin $B_{12}$ patients with and without IF-blocking antibodies and high vitamin $B_{12}$ CML patients be used to assure that the above objectives are met.

Based on these teachings, other types of compositions and related techniques can be readily determined and applied to the practice of the present invention.

The foregoing and other objects, features and advantages of the invention will be apparent from the following more particular description of preferred embodiments of the invention.

DETAILED DESCRIPTION OF THE INVENTION

Based on the problems which are not adequately recognized or dealt with in currently published no-boil vitamin $B_{12}$ and/or folate assays, and a careful analysis of these problems using a large number of test samples, procedures and compositions have been developed in the present invention which compositions and procedures avoid the problems even though they are not recognized or dealt with in currently published no-boil vitamin $B_{12}$ RID assays.

The preferred compositions of the present invention generally include a vitamin $B_{12}$ analogue to be added to samples undergoing no-boil vitamin $B_{12}$ or RID assay. The vitamin $B_{12}$ analogue combines with endogenous binding protein in the sample whether released from the sample vitamin $B_{12}$ or otherwise present in the to-be-assayed sample. By binding, and thus inhibiting this endogenous binding protein with added vitamin $B_{12}$ analogue, the endogenous binding protein is unavailable to combine with radioactive vitamin $B_{12}$ and/or to recombine with vitamin $B_{12}$. Therefore, the errors which would be caused by such a binding combination or recombination are avoided. The added vitamin $B_{12}$ analogue should be one that is not substantially bound by intrinsic factor and thereby does not substantially interefere with the ability of intrinsic factor to bind radioactive vitamin $B_{12}$ and vitamin $B_{12}$ in the to-be-assayed sample. Vitamin $B_{12}$ analogues useful in the practice of the present invention include, but are not limited to, cobinamide (Cbi), CN-Cbl(bde-OH) and (3,5,6,Me3BZA)(CN,OH) Cba, or other vitamin $B_{12}$ analogues. Vitamin $B_{12}$ analogue used should be used at least in an amount great enough to bind substantially all endogenous binding protein which could be expected to be in a sample being prepared for assay. Vitamin $B_{12}$ analogue in the range of about 1 ng to about 10,000 ng per 200 ul of serum sample is useful. Preferred amounts of vitamin $B_{12}$ analogue are in the range of about 20 ng to about 1000 ng per 200 ul of serum sample. The vitamin $B_{12}$ analogue should be added to the to-be-assayed no-boil sample either prior to vitamin $B_{12}$ release, during vitamin $B_{12}$ release or immediately after vitamin $B_{12}$ release, but always prior to or at the same time as the added radioactive vitamin $B_{12}$. By its addition at any of these times the vitamin $B_{12}$ analogue is available to immediately bind endogenous binding protein before it can combine with any substantial amount of released vitamin $B_{12}$ or added radioactive vitamin $B_{12}$. Surprisingly, vitamin $B_{12}$ analogue not only binds endogenous binding protein, but, as subsequently shown in Table I, it also assists in the release of vitamin $B_{12}$ from endogenous binding protein.

A strong base is used in preferred compositions of the no-boil assay of the present invention. It is believed that a strong base, in combination with other ingredients of the present invention, serves to both assist in the release of vitamin $B_{12}$ from endogenous binding protein and also serves to assist in substantially destroying and/or inactivating both the endogenous binding protein, and any intrinsic factor-blocking antibodies which may be present in the sample. The amount of base used should be enough, in combination with the other ingredients, to release substantially all of the vitamin $B_{12}$ and/or folate from endogenous binding protein, to destroy and/or inactivate substantially all of the endogenous binding protein, and to inhibit or destroy substantially all of the intrinsic factor-blocking antibodies. Preferred strong bases include, but are not limited to, NaOH, KOH, LiOH and other strong bases. Useful concentrations of base are in the range of about 0.02 N to about 4.0 N, during the preparation of samples for assay, that is prior to the steps involving partial neutralization and the addition of intrinsic factor (IF) or binding protein that is substantially specific for binding vitamin $B_{12}$ and/or folate. Preferred concentrations of base are in the range of about 0.3 N to 1.0 N during the preparation of samples for assay. The base is preferrably added to the sample at the time the action to prepare the sample for assay is initiated.

At least one additional compound to assist in releasing vitamin $B_{12}$ from endogenous binding protein and to assist in substantially destroying endogenous binding protein and IF-blocking antibodies is included in preferred compositions of the present no-boil assay preparation. The additional compound is preferably selected for its protein destroying character. One family of disulfide protein destroying materials are the sulfhydral compounds. Included within the family of useful sulfhydral compounds are betamercaptoethanol (BME), thioglycolate, thioglycerol and dithiothreitol (DTT), although other sulfhydral compounds or other protein destroying materials may be used in the practice of the present invention. The amount of protein destroying material used should be enough, in combination with the other ingredients, to release substantially all of the vitamin $B_{12}$ from endogenous binding protein, to destroy and/or inactivate substantially all of the endogenous protein, and to inhibit or destroy substantially all of the intrinsic factor-blocking antibodies. Useful concentrations of sulfhydral compounds are in the range of about 0.004 N to 0.4 N during the preparation of samples for assay. Preferred concentrations of sulfhydral compounds are in the range of about 0.04 N to about 0.1 N during the preparation of samples for assay. The protein destroying material is added to the sample at the time the sample is prepared for assay, and preferably prior to, or at the same time as, the radioactive vitamin $B_{12}$ is added to the sample to thus eliminate or minimize the combination of endogenous binding protein with the added radioactive vitamin $B_{12}$.

One preferred vitamin $B_{12}$ assay using the no-boil sample preparation and procedure of the present invention is now described. Generally, the assay procedure is substantially the same as that described in U.S. Pat. No. 4,188,189, with the exception that: (1) the sample and added reagents are not boiled or heated; and (2) additional or substitute compounds, in accordance with the teaching of the present invention are utilized. During the assay the reagents and test specimens are all at ambient room temperature, in the range of about 15° C. to about 35° C. Any reagents or specimens which have been frozen or refrigerated are allowed to come to room temperature. This is not a heating step as the term heating is used herein. To initiate the assay, 200 ul of to-be-tested serum or standard is pipetted into each sample tube, each tube being labelled to indicate its identity. Then, an aqueous 50 ul solution containing:

60 pg $^{57}$Co-$B_{12}$
100 ng cobinamide
10.0 ug KCN
2000.0 ug DTT is added. Now 50 ul of 2.0 N NaOH is pipetted into each tube and after thorough mixing the tubes are allowed to incubate at ambient conditions, without heating, for about 20 minutes. Subsequently the assay is completed when, an aqueous 1000 ul solution having a pH of 6.4 and containing:

0.01 M NaPO4, pH7
0.127 M NaCl
0.162 M boric acid
intrinsic factor in an amount capable of binding about 50 pg of vitamin $B_{12}$ is added to substantially neutralize the solution and allow binding of both sample and radioactive vitamin $B_{12}$ with intrinsic factor (IF). This mixture is then allowed to incubate for about one hour without heating. The simultaneous or subsequent addition of charcoal then results in the unbound vitamin $B_{12}$, in the solution, whether sample or radioactive tracer vitamin $B_{12}$, to be bound to the charcoal, which is subsequently removed from the supernatant liquid. The radioactive count of either the supernatant, which now contains sample vitamin $B_{12}$ and tracer radioactive vitamin $B_{12}$ bound to IF binder, or the charcoal which contains remaining unbound sample vitamin $B_{12}$ and unbound radioactive vitamin $B_{12}$, can be utilized to indicate the amount of vitamin $B_{12}$ in the sample undergoing test, using one or more well known and documented techniques. The resulting preferred assay preparation and assay of the present invention gave highly accurate vitamin $B_{12}$ assay results, as verified by comparison with the Corning radioassay mentioned previously as currently being the most highly tested and accurate RID boiling assay.

The foregoing preferred procedures, can be modified in many ways and still remain within the teaching of the present invention which provides techniques and compositions for preparing vitamin $B_{12}$ for assay without recourse to heating or boiling during any step in the procedure. For example, the size of the serum sample or standard can be increased, say doubled, or reduced substantially, without any need to modify the amount of the other sample preparation ingredients. For efficiency, the tracer, endogenous protein and antibody destroying chemicals, vitamin $B_{12}$ analogue, and strong base, or any combination thereof, may all be combined in a single pipetted liquid aliquot and added to the sample simultaneously, within the teaching of the present invention. In a similar manner, and of special interest and use to laboratories which make many vitamin $B_{12}$ assays, various combinations of the tracer, endogenous binding protein and antibody destroying chemicals, vitamin $B_{12}$ analogue, and strong base may be prepared in liquid form, and/or in dry form, for reconstitution with liquid when needed, for use in the teaching of the present invention. Such materials could also be packaged together, for example, as a kit, thus allowing any laboratory to obtain the test materials from an outside source as a package, without the need to maintain individual chemicals and compositions in stock or the need to go through extensive test preparations. In any of the suggested combinations, these materials, other than the radioactive tracer, are those materials which are required to prepare a sample for no-boil vitamin $B_{12}$ assay, in accordance with the teaching of the preferred embodiments of the present invention.

As folate is often tested simultaneously with vitamin $B_{12}$, the foregoing example may be readily modified for the simultaneous testing of folate. For example, the addition of radioactive folate such as 125I-labelled folate at the time the radioactive vitamin $B_{12}$ is added, and folate binder to bind the sample and radioactive folate at the time of the addition of the IF binder. These modifications make the process suitable for the simultaneous assay of vitamin $B_{12}$ and folate, using well known dual assay techniques.

In a similar manner, the process of the present invention may be modified by using its no-boil processes and compositions for the assay of folate alone.

BASIS OF THE PRESENT INVENTION

The compositions and procedures of the present invention, as already noted, have been conceived, and developed and evolved utilizing information and recognizing problems which were either not previously known, and which were apparently not known or considered of importance in currently published no-boil vitamin $B_{12}$ RID assays. These problems, as previously detailed include:

(1) the need for the release of substantially all of the vitamin $B_{12}$ from endogenous binding protein in a to-be-assayed sample in order to obtain accurate vitamin $B_{12}$ measurement;

(2) the need to destroy or inactivate substantially all of the endogenous binding protein whether released from liberated vitamin $B_{12}$ or otherwise present in the to-be-assayed sample. (Previously published no-heat methods allow substantial amounts of endogenous binding protein to survive in some blood samples, which may result in inaccurate assays of vitamin $B_{12}$ in those samples); and (3) the need to destroy or inactivate antibodies naturally present in some samples which antibodies are of the character which could otherwise react with or block intrinsic factor protein used in RID assays. (Such IF-blocking antibodies result in inaccurate assays of vitamin $B_{12}$ in previously published no-heat methods.)

Clearly the non-heating separation of vitamin $B_{12}$ from endogenous binding protein requires compositions which break the binding linkage between the vitamin $B_{12}$ and endogenous binding protein. The use of bases, which are known protein destroying materials, suggests itself. However, a strong base by itself does not release substantially all vitamin $B_{12}$ from endogenous binding protein. Furthermore, a strong base does not, by itself destroy or inactivate substantially all endogenous binding protein. Finally, a strong base does not destroy substantially all IF-blocking antibodies which may be present in a non-heating sample.

With this recognition of the problem, various materials alone and in combination were tested as to their ability to release vitamin $B_{12}$ from endogenous binding protein and destroy or inactivate endogenous binding protein. These materials were tested by applying them alone and in various combinations, to known amount of radioactive $^{57}Co$-$B_{12}$ which has been bound to various forms of endogenous binding protein by preincubation. More specifically, $^{57}Co$-$B_{12}$ was bound to endogenous binding protein in human plasma, which contains two such binding proteins known as R protein (R) and transcobalamin II (TCII), and also bound with R individually and TCII individually. For use as a control sample, $^{57}Co$-$B_{12}$ was also preincubated with buffer solution substantially free of any binding protein.

As set forth in Table I, following the preincubation with radioactive vitamin $B_{12}$ and the subsequent treatment with the individual or combined materials, each sample was substantially neutralized, incubated for 60 minutes, without IF or any added binder, and then treated with charcoal, which adsorbs substantially all of the bound radioactive vitamin $B_{12}$ that is released and remains released from endogenous binding protein. Therefore, using this procedure, the lesser the amount of $^{57}Co$-$B_{12}$ found in the supernatant liquid, as reported for example in Table I, the greater the amount of $^{57}Co$-$B_{12}$ which was released by the material or materials, and the better the materials are in an assay preparation composition.

TABLE 1A

Release of [$^{57}Co$]$B_{12}$ from plasma and various binders

| Sample | Cbi | BME | NaOH | % [$^{57}Co$]$B_{12}$ in supernatant |
|---|---|---|---|---|
| plasma | − | − | − | 94.4 |
| R | − | − | − | 100.0 |
| TC II | − | − | − | 74.3 |
| buffer | − | − | − | 0.4 |
| plasma | + | − | − | 95.9 |
| R | + | − | − | 99.8 |
| TC II | + | − | − | 76.1 |
| buffer | + | − | − | 0.1 |
| plasma | − | + | − | 44.9 |
| R | − | + | − | 100.0 |
| TC II | − | + | − | 83.7 |
| buffer | − | + | − | 0.3 |
| plasma | − | − | + | 40.8 |
| R | − | − | + | 31.3 |
| TC II | − | − | + | 6.0 |
| buffer | − | − | + | 0.3 |
| plasma | + | + | − | 71.1 |
| R | + | + | − | 100.0 |
| TC II | + | + | − | 84.8 |
| buffer | + | + | − | 0.2 |
| plasma | + | − | + | 26.9 |
| R | + | − | + | 4.4 |
| TC II | + | − | + | 5.0 |
| buffer | + | − | + | 0.0 |
| plasma | − | + | + | 2.5 |
| R | − | + | + | 10.8 |
| TC II | − | + | + | 1.5 |
| buffer | − | + | + | 0.5 |
| plasma | + | + | + | 1.4 |
| R | + | + | + | 0.9 |
| TC II | + | + | + | 1.0 |
| buffer | + | + | + | 0.1 |

As set forth by Table I, the various individual and combined materials had varying effects on the release of $^{57}Co$-$B_{12}$.

Now again, referring to Table IA, when a combination of cobinamide (Cbi), betamencaptoethanol (BME) and NaOH (strong base) were used, for each of Samples 29-32, the lowest percent of $^{57}Co$-$B_{12}$ was found to remain in the supernatant, as compared to all other combinations. Therefore, the greatest release of vitamin $B_{12}$ from binding protein was achieved using these three materials in combination.

Special note is also called to Samples 13-16 in Table I in which a strong base, NaOH was used at a concentration of 0.5 N during the release analysis. It will be noted that in Samples 13-15 substantial amounts of $^{57}Co$-$B_{12}$ remained in the supernatant liquid, and therefore was not released substantially completely by denaturing with a strong base in the absence of other materials. This raises questions as to the effectiveness of a strong base, by itself, as a denaturing agent. It is noted that all solutions had KCN present in them.

Now, taken as a whole, the data in Table I makes it abundantly clear that in a controlled experiment with a known amount of radioactive vitamin $B_{12}$, and no excessive amounts of endogenous binding protein or IF-blocking antibodies, that the combination of Cbi (a vitamin $B_{12}$ analogue), BME (a disulfide protein destroying composition), and NaOH (a strong base) provides the most substantially complete vitamin $B_{12}$ release composition. In a similar manner, the data in Table IB also shows that this same composition also provides substantially complete folate release from endogenous folate binding protein.

Table IIA set forth comparative data as to vitamin $B_{12}$ analysis of a large number of normal subjects using the standard "boiling" techniques of Kolhouse et. al. and Allen, and a prototype non-boiling technique of the present invention, still using BME as the disulfide protein destroying composition. Table IIB contains comparative data for folate analysis for some normal and patient samples. Table IIC contains comparative data for vitamin $B_{12}$ and simultaneous folate analysis on a few normals and two vitamin $B_{12}$ deficient patients. Note the total agreement of results as to the amount of vitamin $B_{12}$, folate, and vitamin $B_{12}$ and folate, using both the boil and the no-boil techniques, which is well within both scientific and clinical tolerances.

TABLE 1B

Release of $^{125}$I—folate from Serum

| Serum* | % $^{125}$I—folate in supernatant | |
|---|---|---|
| | Treated** | Untreated*** |
| A | 2.6 | 82.9 |
| B | 1.7 | 45.4 |
| C | 3.2 | 97.0 |
| D | 1.8 | 57.6 |
| E | 2.2 | 74.9 |
| F | 1.9 | 74.6 |
| G | 1.5 | 52.4 |

*These sera had high endogenous folate binding protein levels. Most normal sera have no free endogenous folate binding ability, i.e. untreated is <2%.
**Same as in Table 1A - complete conditions.
***Neutralizing solution, i.e. Tris-HCl, was added before Cbi, BME & NaOH.

Assay Conditions for Table I
A. These assays had sample volumes of 200 ul and were incubated at room temperature for 20 minutes with 45.4 pg CO$^{57}$B$_{12}$ in 5 ul of H$_2$O. The samples were: (a) 40 ul Buffer A (.05 M KPO$_4$ pH 7.5, .5 M NaCl, 150 mg HSA/ml) plus 160 ul .15 M NaCl); (b) 200 ul plasma; (c) 40 ul salivary R protein (1.2 ng B$_{12}$ binding ability) plus 40 ul Buffer A plus 120 ul saline; (d) 160 ul TC II (0.59 ng B$_{12}$ binding ability) plus 40 ul Buffer A. Following this incubation 25 ug of KCN was added in 5 ul of H$_2$O to every test tube and eight different conditions were introduced. (See Table 1) They were all possible combinations of the following: (a) 1 ug cobinamide in 5 ul of H$_2$O; (b) 40 ul of 1 M BME; and (c) 100 ul of 2 N NaOH. H$_2$O was added when an ingredient(s) was missing. The reaction, in a volume of 355 ul, was allowed 20 minutes at room temperature before neutralizing those tubes containing NaOH with 275 ul 1 M Tris-HCl pH 7.5. All the test tubes had their volume brought up to 1.5 ml with 0.1 M NaCl and the assay went through a final 60 minutes at room temperature. The reaction was ended with 0.5 ml BSA coated charcoal. The assay tubes were spun 10,000 × g for 20 minutes and 1.0 ml supernatant was removed for counting.
B. The complete assay was also used to investigate $^{125}$I—folate release.

TABLE IIA

Serum $B_{12}$ values for normals using boiling and non-boiling methods.

| Serum Normal: | Serum $B_{12}$ (pg/ml) | |
|---|---|---|
| | Boiled | Non-boiled |
| 1. | 390 | 350 |
| 2. | 260 | 319 |
| 3. | 230 | 258 |
| 4. | 325 | 419 |
| 5. | 475 | 510 |
| 6. | 365 | 465 |
| 7. | 205 | 242 |
| 8. | 540 | 590 |

TABLE IIA-continued

Serum $B_{12}$ values for normals using boiling and non-boiling methods.

| Serum Normal: | Serum $B_{12}$ (pg/ml) | |
|---|---|---|
| | Boiled | Non-boiled |
| 9. | 410 | 527 |
| 10. | 390 | 496 |
| 11. | 150 | 211 |
| 12. | 636 | 490 |
| 13. | 300 | 357 |
| 14. | 460 | 589 |
| 15. | 390 | 490 |
| 16. | 305 | 316 |
| 17. | 265 | 326 |
| 18. | 370 | 420 |
| 19. | 200 | 292 |
| 20. | 325 | 235 |
| 21. | 230 | 290 |
| 22. | 295 | 382 |
| 23. | 425 | 546 |
| 24. | 700 | 785 |
| 25. | 280 | 310 |
| 26. | 165 | 171 |
| 27. | 200 | 254 |
| 28. | 185 | 220 |
| 29. | 150 | 223 |
| 30. | 325 | 413 |
| 31. | 345 | 440 |
| 32. | 170 | 208 |
| 33. | 410 | 468 |
| 34. | 300 | 378 |
| 35. | 480 | 518 |
| 36. | 230 | 298 |
| 37. | 230 | 245 |
| 38. | 345 | 363 |
| 39. | 250 | 319 |
| 40. | 300 | 335 |
| 41. | 250 | 304 |
| 42. | 500 | 580 |
| 43. | 240 | 261 |

TABLE IIB

Serum folate values in patients on whom folate values were requested in Colorado General Hospital boiling versus non-boiling assays

| Serum | serum folate (ng/ml) | |
|---|---|---|
| | boiled* | non-boiled |
| 1 | 6.1 | 6.8 |
| 2 | 3.3 | 2.6 |
| 3 | 22.0 | 16.3 |
| 4 | 7.6 | 7.2 |
| 5 | 2.8 | 2.5 |
| 6 | 20.0 | 35.7 |
| 7 | 2.5 | 1.6 |
| 8 | 12.0 | 10.8 |
| 9 | 4.5 | 4.7 |
| 10 | 11.0 | 10.3 |
| 11 | 3.4 | 4.0 |
| 12 | 3.4 | 4.0 |
| 13 | 5.9 | 9.3 |
| 14 | 3.0 | 3.5 |
| 15 | 10.0 | 6.9 |
| 16 | 23.0 | 20.5 |
| 17 | 11.5 | 8.8 |
| 18 | 2.1 | 2.5 |
| 19 | 3.4 | 3.0 |
| 20 | 3.1 | 3.2 |
| 21 | 8.6 | 8.2 |
| 22 | 4.5 | 4.6 |
| 23 | 3.3 | 4.0 |
| 24 | 13.5 | 15.6 |
| 25 | 6.1 | 6.2 |
| 26 | 8.5 | 8.0 |
| 27 | 3.2 | 3.0 |
| 28 | >25.0 | 28.0 |
| 29 | 23.0 | 18.8 |
| 30 | 11.5 | 8.4 |
| 31 | 3.3 | 2.6 |

TABLE IIB-continued

Serum folate values in patients on whom folate values were requested in Colorado General Hospital boiling versus non-boiling assays

| Serum | serum folate (ng/ml) | |
|---|---|---|
| | boiled* | non-boiled |
| 32 | 15.0 | 17.2 |

*Becton-Dickinson kit in our hospital lab. (normal range = 3–5 ng/ml)

TABLE IIC

Separate versus combined assays for Vitamin $B_{12}$ and folate using the non-boiling technique.

| | Separate Assays | | Combined Assays | |
|---|---|---|---|---|
| Set A | folate ng/ml | $B_{12}$ pg/ml | folate ng/ml | $B_{12}$ pg/ml |
| 1 | 12.8 | 245 | 11.5 | 190 |
| 2 | 8.5 | 360 | 9.2 | 305 |
| 3 | 17.2 | 300 | 14.1 | 260 |
| 4 | 15.2 | 200 | 16.4 | 185 |
| 5 | 16.2 | 400 | 16.0 | 370 |
| 6 | 5.8 | 320 | 5.2 | 360 |
| 7 | 15.5 | 340 | 11.5 | 270 |
| 8 | 7.6 | <10 | 7.4 | <10 |
| 9 | 23.0 | 80 | 23.0 | 40 |

This supports the accuracy and utility of the compositions of the present invention for testing vitamin $B_{12}$ and/or folate in normal subjects and in some vitamin $B_{12}$ deficient patients.

Table III is of interest as showing the application of a "boiling" and one prototype non-boiling technique of the present invention to samples from a larger number of known vitamin $B_{12}$ deficient patients. But for serum Sample #17, the agreement achieved by both techniques is statistically excellent, again showing the scientific accuracy and utility of the present invention. However, the large discrepency in serum Sample #17 is clinically unacceptable. Using the assay data from this prototype "non-boiled" assay of the present invention would have resulted in the patient who was the source of Sample #17 being classified "normal". Therefore, the prototype "no-boil" assay of Sample #17 represents a clinically unacceptable lapse in this prototype composition and technique. The failure to diagnose this single patient correctly could have led to a failure to treat this patient with vitamin $B_{12}$. This could have had disastrous consequences for this patient since untreated vitamin $B_{12}$ deficiency can lead to potentially fatal blood and/or neurologic abnormalities, with the latter being especially serious since frequently they cannot be reversed by later treatment with vitamin $B_{12}$, possibly resulting in commitment to a mental institution for life.

Subsequent analysis indicated that many of the "deficient" samples set forth in Table III, including Sample #17, had IF-blocking antibodies (which have been labelled "anti-IF blocking antibody" in Table III). In Table III "+" indicates the presence and "—" indicates the absence of such antibodies. Further analysis indicated that Sample #17 had only a moderately high amount of IF blocking antibodies, but more importantly, that its antibodies were particularly resistant to destruction by the prototype assay composition used. (IF-blocking antibodies have many different structures and thus differ in their resistance to destruction.) It was also determined that these IF-blocking antibodies compete with vitamin $B_{12}$ for IF in the test.

TABLE III

Serum $B_{12}$ values for patients with clinical evidence of $B_{12}$ deficiency using boiling and non-boiling methods.

| | Serum $B_{12}$(pg/ml) | | anti IF |
|---|---|---|---|
| Serum | boiled | non-boiled | blocking antibody |
| 1. | 41 | <10 | + |
| 2. | 48 | 16 | — |
| 3. | 53 | 55 | — |
| 4. | 48 | <10 | + |
| 5. | 31 | 34 | + |
| 6. | 54 | 39 | — |
| 7. | 50 | <10 | + |
| 8. | <10 | <10 | — |
| 9. | 25 | <10 | — |
| 10. | 75 | 33 | + |
| 11. | <10 | <10 | + |
| 12. | 16 | 31 | + |
| 13. | 51 | 60 | — |
| 14. | 39 | 59 | — |
| 15. | 24 | 38 | — |
| 16. | <10 | 13 | + |
| **17. | 52 | 290 | + |
| 18. | 18 | 61 | — |
| 19. | 22 | 59 | — |
| 20. | <10 | <10 | — |
| 21. | 70 | 35 | + |
| 22. | 10 | 30 | — |
| 23. | 95 | 113 | — |
| 24. | <10 | <10 | — |
| 25. | 60 | 75 | — |
| 26. | 85 | 104 | — |
| 27. | <10 | <10 | — |
| 28. | 43 | 60 | — |
| 29. | 32 | 45 | — |
| 30. | 39 | 68 | — |
| 31. | 44 | 15 | — |
| 32. | 38 | 49 | — |
| 33. | <10 | 24 | — |
| 34. | <10 | <10 | — |
| 35. | <10 | 34 | — |
| 36. | 28 | <10 | — |
| 37. | <10 | <10 | + |
| 38. | 70 | 55 | — |
| 39. | 42 | 68 | — |
| 40. | 58 | 56 | — |
| 41. | 38 | <10 | + |
| 42. | <10 | <10 | — |
| 43. | <10 | 19 | — |

**high value by non-boiling is due to incomplete destruction of anti-IF antibody.

Thus, when not destroyed or inhibited, the antibodies make amounts of IF unavailable to bind with sample and radioactive vitamin $B_{12}$, which unavailability in turn causes an inaccurate, smaller amount of vitamin $B_{12}$ and radioactive $B_{12}$ to be bound by IF which in turn results in a lower radioactive count in the IF-containing supernatant. This lower count is then interpreted as the presence of additional vitamin $B_{12}$ in the sample, while what was really present was IF-blocking antibodies. Therefore, a different composition, capable of destroying substantially all IF-blocking antibodies, when such antibodies are present in any sample, was devised.

Reconstitution of the prototype composition of the present invention to include a stronger disulfide protein destroying material, DTT, instead of BME, results in a composition which is more effective in destroying IF blocking antibodies. Using such a DTT modified composition, and retesting some of the samples in Table III, resulted in substantially the same vitamin $B_{12}$ analysis of the samples, with the exception that Sample #17 now showed a low vitamin $B_{12}$ content of 55 pg/ml. In retrospect, it appears that classic boiling techniques apparently destroy both endogenous binding protein and IF-blocking antibodies when they are present in a sample, but that "no-boil" chemical techniques may release vitamin $B_{12}$ from endogenous binding protein without destroying or inactivating either substantially all endogenous binding protein or substantially all IF-blocking antibodies. These problems are now overcome by the preferred compositions and no-boil procedures of the present invention which release substantially all vitamin $B_{12}$ for assay, which destroy substantially all endogenous binding protein, which bind or inhibit substantially all undestroyed endogenous binding protein, and which destroy or inhibit substantially all IF-blocking antibodies.

SUPPORTING DATA

With the initial recognition of the problems of no-boil analysis of vitamin $B_{12}$, including the need for: full release of substantially all vitamin $B_{12}$; and for the first time the destruction or inactivation of substantially all endogenous binding protein; then the conception of a prototype solution; its reduction to practice followed by the recognition of another problem and the identification of that problem as being related to the presence of IF-blocking antibodies in some of the samples, and therefore the need for the destruction or inactivation of substantially all such IF-blocking antibodies which may be in any sample; then the compositions and procedures of the preferred embodiments of the present invention were reformulated and again reduced to practice, with the result being an apparently highly accurate vitamin $B_{12}$ and/or folate no-boil RID assay.

Steps and procedures were then taken to check the accuracy and validity of the preferred embodiments of the present invention. Referring to Table IV, which is similar to Table I, a "non-specific binding" comparison was made between the highly accurate reference Corning boil assay and the no-boil assay of the present invention. "Non-specific binding" is a test of the ability of the samples to bind $^{57}Co$-$B_{12}$ following the release process of either the Corning reference assay or follownng the release process of the present invention. Effectively a Corning reference boil or the no-boil procedure of the present invention were carried out, except that in each instance a blank reagent was substituted for the IF binders. The subsequent use of charcoal to separate unbound vitamin $B_{12}$ and unbound radioactive vitamin $B_{12}$ from vitamin $B_{12}$ and radioactive vitamin $B_{12}$ bound to endogenous binding protein gave "non-specific binding" defined as:

% Non-specific binding =

$$\frac{\text{Sample blank counts} - \text{assay blank counts}}{\text{Total counts} - \text{assay blank counts}} \times 100$$

Now referring to Table IV, it is seen that the no-boil assay of the present invention not only agrees with the Corning reference assay for: Normal vitamin $B_{12}$ subjects; and deficient (Low) vitamin $B_{12}$ patients, without antibodies (Antibody Negative); but also for subjects known to be suffering from chronic myelogenous leukemia (CML), a disease which usually produces subjects with both extremely high vitamin $B_{12}$ levels and extremely high levels of endogenous binding protein. More specifically, the non-specific binding of the present invention actually appears to be superior to the Corning reference analysis, as indicated by a comparison of the mean for each group.

The "Unsaturated $B_{12}$-Binding Ability" in Table IV, indicates the amount of endogenous binding protein in the initial samples which is not bound to endogenous vitamin $B_{12}$. Such unbound endogenous binding protein may interfere with the accuracy of an assay which does not destroy or inhibit substantially all endogenous binding protein.

TABLE IV

Comparison of Non-Specific Binding Using the Reference Boil Assay and the No-Boil Assay of the Present Invention

| Subject or Patient (#) | Unsaturated $B_{12}$-Binding Ability (pg/ml) | Non-Specific Binding | |
|---|---|---|---|
| | | Corning Reference Boil Assay (%) | No-Boil Assay of the Present Invention (%) |
| Normal | | | |
| 1 | 470 | 2.3 | 1.3 |
| 4 | 360 | 2.4 | 1.2 |
| 6 | 170 | 2.6 | 1.4 |
| 12 | 100 | 2.4 | 1.0 |
| 20 | 710 | 3.0 | 1.1 |
| 21 | 520 | 2.2 | 1.1 |
| 30 | 340 | 1.7 | 1.0 |
| 36 | 230 | 1.8 | 1.0 |
| 39 | 580 | 1.3 | 1.2 |
| 40 | 920 | 2.5 | 1.4 |
| 41 | 2,400 | 3.2 | 1.3 |
| 43 | 560 | 2.8 | 1.2 |
| 45 | 920 | 3.1 | 1.3 |
| 49 | 160 | 1.7 | 0.9 |
| Mean | 603 | 2.4 | 1.2 |
| Low $B_{12}$, Antibody Negative | | | |
| 1 | 870 | 2.2 | 0.6 |
| 2 | 2,600 | 2.1 | 1.4 |
| 3 | 1,300 | 2.2 | 1.2 |
| 4 | 2,300 | 1.9 | 0.8 |
| 5 | 1,400 | 1.7 | 0.8 |
| 6 | 850 | 2.6 | 1.2 |
| 7 | 1,800 | 1.7 | 0.9 |
| 8 | 1,400 | 1.7 | 1.2 |
| 9 | 1,100 | 1.9 | 1.2 |
| 10 | 1,200 | 1.5 | 0.9 |
| 11 | 900 | 1.5 | 1.0 |
| 12 | 1,100 | 3.3 | 1.4 |
| Mean | 1,402 | 2.0 | 1.0 |
| Chronic Myelogenous Leukemia | | | |
| 1 | 2,400 | 3.9 | 1.7 |
| 2 | 3,200 | 4.5 | 1.7 |
| 3 | 4,500 | 6.3 | 2.1 |
| 4 | 1,200 | 3.9 | 1.5 |
| 5 | 3,900 | 6.0 | 2.3 |
| 6 | 17,000 | 12.4 | 7.4 |
| 7 | 2,000 | 9.1 | 6.5 |
| 8 | 1,800 | 5.3 | 2.1 |
| 9 | 14,000 | 3.1 | 2.7 |
| 10 | 3,500 | 6.7 | 2.7 |
| 11 | 15,000 | 4.0 | 2.5 |
| 12 | 860 | 2.2 | 1.2 |
| 13 | 15,000 | 4.2 | 2.4 |
| 14 | 7,900 | −0.3 | 0.4 |
| 15 | 15,000 | 4.4 | 3.4 |
| 16 | 7,100 | 0.0 | 0.8 |
| 17 | 7,300 | 0.6 | 2.2 |
| 18 | 7,400 | −2.1 | 0.4 |
| Mean | 7,170 | 4.1 | 2.4 |

Table V is a relatively straight forward comparison between a large number of normal subjects (50) who should have normal vitamin $B_{12}$ levels, using both the Corning Reference assay and the no boil assay of the preferred embodiment of the present invention. It is similar to Table II, but the samples used in Table II and in Table V were not the same. Both the scientific and clinical agreement using both assays is excellent for each and every sample assayed and for the mean of all the samples. It should be noted that Table V also defines a "Normal" vitamin $B_{12}$ range using the preferred processes and compositions of the present invention. This Normal range is defined as "140–704 pg/ml", as compared to "148–696 pg/ml" for the Reference assay, mathematically and scientifically an insignificant difference.

Table VI sets forth a comparison between known vitamin $B_{12}$ deficient samples without antibodies, using the Reference assay and the no-boil assay of the present invention. Again, both assays produce results which are scientifically and clinically in complete agreement. All samples were found to be "below the normal range" using both techniques, and the mean from both assays was exactly the same. This is a strong confirmation of the accuracy of the present invention in its ability to identify vitamin $B_{12}$ in vitamin $B_{12}$ deficient subjects, in the absence of IF-blocking antibodies.

Table VII is of extremely great interest as supporting the present invention's accuracy when used to identify subjects with low vitamin $B_{12}$ who have IF-blocking antibodies in their blood serum. In this table, the "Capacity to Block vitamin $B_{12}$ binding to IF" is an indicator of the amount of IF which could and would be bound by IF-blocking antibodies present initially in the serum. This ranges from a low of 600 pg/ml, for sample 76, to a high of 360,000 pg/ml for sample 96, with a mean of 29,000 pg/ml. Now despite the varied, and often extremely high levels of IF-blocking antibodies in these samples, there is complete agreement between the reference assay and the assay of the present invention in identifying each and every sample, 100% of the samples, as being vitamin $B_{12}$ deficient. More specifically, the vitamin $B_{12}$ value obtained with the present invention actually appears to be superior to the reference assay as indicated by a comparison of the mean for each group.

TABLE V

Comparison of Serum Vitamin $B_{12}$ Values in 50 Normal Subjects Using the Reference Boil Assay and the No-Boil Assay of the Present Invention

| Normal Subjects (#) | Corning Reference Boil Assay (pg/ml) | No-Boil Assay of the Present Invention (pg/ml) |
|---|---|---|
| 1 | 243 | 180 |
| 2 | 322 | 365 |
| 3 | 343 | 267 |
| 4 | 273 | 265 |
| 5 | 350 | 450 |
| 6 | 430 | 410 |
| 7 | 225 | 172 |
| 8 | 270 | 225 |
| 9 | 429 | 320 |
| 10 | 303 | 203 |
| 11 | 730 | 690 |
| 12 | 397 | 375 |
| 13 | 182 | 192 |
| 14 | 234 | 250 |
| 15 | 330 | 330 |
| 16 | 397 | 420 |
| 17 | 455 | 435 |
| 18 | 181 | 186 |
| 19 | 363 | 340 |
| 20 | 360 | 320 |
| 21 | 175 | 130 |
| 22 | 220 | 203 |
| 23 | 540 | 510 |
| 24 | 345 | 343 |
| 25 | 338 | 373 |
| 26 | 303 | 297 |
| 27 | 385 | 345 |
| 28 | 400 | 445 |
| 29 | 360 | 340 |
| 30 | 580 | 550 |
| 31 | 197 | 180 |
| 32 | 795 | 790 |
| 33 | 380 | 380 |
| 34 | 442 | 427 |
| 35 | 465 | 450 |
| 36 | 232 | 250 |
| 37 | 308 | 350 |
| 38 | 250 | 250 |
| 39 | 193 | 245 |
| 40 | 322 | 285 |
| 41 | 385 | 365 |
| 42 | 162 | 200 |
| 43 | 215 | 180 |
| 44 | 352 | 500 |
| 45 | 700 | 740 |
| 46 | 218 | 163 |
| 47 | 377 | 323 |
| 48 | 233 | 250 |
| 49 | 450 | 520 |
| 50 | 150 | 161 |
| Mean | 346 | 339 |
| Normal Range[a] | 148–696 | 140–704 |

[a] Mean ± 2 standard deviations after log normalization to correct for skewness of the data to higher values.

TABLE VI

Comparison of Serum Vitamin $B_{12}$ Values in 12 Patients Without Anti-IF Blocking Anitbodies Using the Reference Boil Assay and the No-Boil Assay of the Present Invention

| Low $B_{12}$, Antibody Negative Patients (#) | Corning Reference Boil Assay (pg/ml) | No-Boil Assay of the Present Invention (pg/ml) |
|---|---|---|
| 1 | 18 | 65 |
| 2 | 128 | 120 |
| 3 | 108 | 25 |
| 4 | 120 | 100 |
| 5 | 5 | 38 |
| 6 | 92 | 99 |
| 7 | 77 | 89 |
| 8 | 78 | 103 |
| 9 | 107 | 103 |
| 10 | 117 | 117 |
| 11 | 80 | 104 |
| 12 | 88 | 98 |
| Mean | 85 | 85 |
| Number of patients below the normal range | (12) | (12) |
| % of patients below the normal range | (100%) | (100%) |

TABLE VII

Comparison of Serum Vitamin $B_{12}$ Values in 111 Patients with Anti-IF Blocking Antibodies Using the Reference Boil Assay and the No-Boil Assay of the Present Invention

| Low $B_{12}$, Antibody Positive Patients (#) | Capacity to Block $B_{12}$ Binding to IF (pg/ml) | Serum Vitamin $B_{12}$ Values | |
|---|---|---|---|
| | | Corning Reference Boil Assay (pg/ml) | No Boil Assay of the Present Invention (pg/ml) |
| 1 | 200,000 | 0 | 0 |
| 2 | 17,000 | 0 | 24 |
| 3 | 21,000 | 110 | 120 |
| 4 | 18,000 | 0 | 20 |
| 5 | 24,000 | 0 | 0 |
| 6 | 1,300 | 0 | 5 |
| 7 | 2,300 | 70 | 120 |
| 8 | 21,000 | 0 | 16 |
| 9 | 1,000 | 39 | 75 |
| 10 | 4,900 | 0 | 19 |
| 11 | 6,400 | 0 | 26 |
| 12 | 6,400 | 0 | 60 |
| 13 | 15,000 | 30 | 60 |
| 14 | 23,000 | 0 | 0 |
| 15 | 25,000 | 15 | 25 |
| 16 | 3,600 | 83 | 90 |
| 17 | 4,200 | 47 | 40 |
| 18 | 15,000 | 0 | 19 |
| 19 | 1,200 | 100 | 28 |
| 20 | 2,400 | 13 | 0 |
| 21 | 1,200 | 86 | 24 |
| 22 | 1,200 | 15 | 0 |
| 23 | 22,000 | 106 | 84 |
| 24 | 1,400 | 80 | 24 |
| 25 | 1,500 | 117 | 31 |
| 26 | 1,100 | 5 | 5 |
| 27 | 8,700 | 99 | 78 |
| 28 | 700 | 69 | 5 |
| 29 | 6,400 | 5 | 0 |
| 30 | 25,000 | 33 | 0 |
| 31 | 5,100 | 25 | 34 |
| 32 | 26,000 | 91 | 62 |
| 33 | 25,000 | 38 | 18 |
| 34 | 5,800 | 72 | 60 |
| 35 | 2,500 | 29 | 19 |
| 36 | 6,400 | 5 | 0 |
| 37 | 4,700 | 76 | 56 |
| 38 | 3,600 | 44 | 42 |
| 39 | 2,300 | 28 | 18 |
| 40 | 7,700 | 0 | 0 |
| 41 | 23,000 | 5 | 5 |
| 42 | 9,000 | 41 | 18 |
| 43 | 18,000 | 24 | 19 |
| 44 | 27,000 | 29 | 0 |
| 45 | 3,900 | 122 | 68 |
| 46 | 1,800 | 142 | 135 |
| 47 | 4,300 | 5 | 0 |
| 48 | 2,400 | 125 | 110 |
| 49 | 18,000 | 35 | 22 |
| 50 | 4,200 | 38 | 0 |
| 51 | 42,000 | 22 | 10 |
| 52 | 4,000 | 18 | 0 |
| 53 | 50,000 | 36 | 0 |
| 54 | 25,000 | 33 | 0 |
| 55 | 4,400 | 29 | 20 |
| 56 | 21,000 | 28 | 11 |
| 57 | 5,500 | 100 | 118 |
| 58 | 33,000 | 23 | 0 |
| 59 | 4,200 | 31 | 61 |
| 60 | 3,700 | 54 | 39 |
| 61 | 140,000 | 25 | 7 |
| 62 | 4,100 | 31 | 26 |
| 63 | 210,000 | 70 | 86 |
| 64 | 5,500 | 90 | 33 |
| 65 | 20,000 | 26 | 5 |
| 66 | 3,600 | 47 | 48 |
| 67 | 67,000 | 33 | 18 |
| 68 | 4,400 | 51 | 37 |
| 69 | 4,100 | 74 | 47 |
| 70 | 170,000 | 33 | 40 |
| 71 | 10,000 | 0 | 5 |
| 72 | 12,000 | 25 | 20 |
| 73 | 12,000 | 40 | 28 |

TABLE VII-continued

Comparison of Serum Vitamin $B_{12}$ Values in 111 Patients with Anti-IF Blocking Antibodies Using the Reference Boil Assay and the No-Boil Assay of the Present Invention

| Low $B_{12}$, Antibody Positive Patients (#) | Capacity to Block $B_{12}$ Binding to IF (pg/ml) | Serum Vitamin $B_{12}$ Values | |
|---|---|---|---|
| | | Corning Reference Boil Assay (pg/ml) | No Boil Assay of the Present Invention (pg/ml) |
| 74 | 200,000 | 55 | 36 |
| 75 | 1,400 | 10 | 13 |
| 76 | 600 | 30 | 20 |
| 77 | 10,000 | 79 | 40 |
| 78 | 19,000 | 123 | 94 |
| 79 | 1,500 | 10 | 5 |
| 80 | 2,300 | 27 | 27 |
| 81 | 8,700 | 41 | 44 |
| 82 | 2,900 | 46 | 40 |
| 83 | 260,000 | 39 | 10 |
| 84 | 800 | 78 | 48 |
| 85 | 7,700 | 110 | 15 |
| 86 | 2,900 | 96 | 32 |
| 87 | 800 | 45 | 29 |
| 88 | 180,000 | 125 | 102 |
| 89 | 2,700 | 10 | 15 |
| 90 | 6,400 | 16 | 14 |
| 91 | 21,000 | 0 | 5 |
| 92 | 4,400 | 115 | 57 |
| 93 | 2,200 | 94 | 51 |
| 94 | 8,700 | 92 | 48 |
| 95 | 320,000 | 5 | 0 |
| 96 | 360,000 | 23 | 13 |
| 97 | 1,000 | 68 | 0 |
| 98 | 17,000 | 24 | 5 |
| 99 | 1,400 | 106 | 31 |
| 100 | 3,000 | 36 | 0 |
| 101 | 22,000 | 5 | 0 |
| 102 | 2,900 | 36 | 42 |
| 103 | 2,900 | 39 | 21 |
| 104 | 2,400 | 35 | 0 |
| 105 | 900 | 130 | 93 |
| 106 | 20,000 | 33 | 19 |
| 107 | 900 | 25 | 13 |
| 108 | 2,700 | 46 | 0 |
| 109 | 2,900 | 57 | 19 |
| 110 | 54,000 | 70 | 40 |
| 111 | 140,000 | 41 | 37 |
| Mean | 29,000 | 45 | 31 |
| Number of patients below normal range | | (111) | (111) |
| % of patients below normal range | | (100%) | (100%) |

It is therefore clear that using the preferred embodiments of the present invention, the no-boil assay of the present invention is not rendered ineffective or inoperative as to any sample by the presence of IF blocking antibodies.

Now referring to Table VIII, a substantial number of samples from CML patients were tested using both the reference assay and the assay of the present invention. As there is some indication, which will be detailed below, that some no-boil assays may be sample concentration sensitive, both "Standard" sample concentrations and "Diluted" sample concentrations were run for both assays. Reviewing the information set forth in Table VIII, it is again seen that the assay of the present invention is completely in agreement with the reference assay. In the single instance, Patient #12, in which a CML patient was determined to be in a normal vitamin $B_{12}$ range by the reference assay, the present no-boil assay also identified that, and only that, subject as being normal.

As noted in the prior art discussion, there are currently two known "no-boil" assays now being marketed, one from each of RIA and Diagnostic Products. Table IX sets forth comparisons of the Non-Specific Binding Character of each of these commercial no-boil assays, with the "Corning Reference Boil Assay" for a number of "Normal" vitamin $B_{12}$ subjects, a number of known vitamin $B_{12}$ deficient subjects without antibodies (Low $B_{12}$, antibody negative) and a number of CML subjects. The results set forth in Table IX indicate that the no-boil RIA and Diagnostic Products tests are completely accurate in destroying endogenous binding protein, as measured by non-specific binding in samples from normal and deficient subjects without IF-blocking antibodies. However, both of those commercial kits failed to destroy, or inhibit or block endogenous binding protein in samples from CML patients, as measured by non-specific binding, and as compared to both the procedure of the Reference assay and the procedure of the present invention as set forth in Table IV for the same CML subjects. Therefore, the no-boil procedure of the present invention is more accurate, at least as to CML patients, than existing commercial no-boil kits, when all are compared to the Corning boil assay as a reference.

TABLE VIII

Comparison of Serum Vitamin $B_{12}$ Values in 29 Patients with Chronic Myelogenous Leukemia Using the Reference Boil Assay and the No-Boil Assay of the Present Invention

| Chronic Myelogenous Leukemia Patients (#) | Serum Vitamin $B_{12}$ Values | | | |
|---|---|---|---|---|
| | Corning Reference Boil Assay Volume Assayed | | No-Boil Assay of the Present Invention Volume Assayed | |
| | Standard (pg/ml) | Diluted (pg/ml) | Standard (pg/ml) | Diluted (pg/ml) |
| 1 | >2,000 | 4,100 | >2,000 | 4,200 |
| 2 | >2,000 | 3,500 | >2,000 | 2,700 |
| 3 | >2,000 | 2,300 | 1,900 | 1,700 |
| 4 | >2,000 | 3,300 | >2,000 | 2,600 |
| 5 | >2,000 | 4,400 | >2,000 | 4,600 |
| 6 | >2,000 | 7,500 | >2,000 | 8,600 |
| 7 | >2,000 | 14,000 | >2,000 | 17,000 |
| 8 | >2,000 | 4,700 | >2,000 | 4,800 |
| 9 | >2,000 | 6,300 | >2,000 | 7,000 |
| 10 | >2,000 | 5,000 | >2,000 | 6,100 |
| 11 | >2,000 | 6,300 | >2,000 | 6,600 |
| 12 | 460 | 500 | 410 | 450 |
| 13 | >2,000 | 6,800 | >2,000 | 7,600 |
| 14 | >2,000 | 6,300 | >2,000 | 7,400 |
| 15 | >2,000 | 5,800 | >2,000 | 5,700 |
| 16 | >2,000 | 6,600 | >2,000 | 7,500 |
| 17 | >2,000 | 8,500 | >2,000 | 10,000 |
| 18 | >2,000 | 4,900 | >2,000 | 5,900 |
| 19 | >2,000 | 13,000 | >2,000 | 15,000 |
| 20 | >2,000 | 4,700 | >2,000 | 4,900 |
| 21 | >2,000 | 16,000 | >2,000 | 18,000 |
| 22 | >2,000 | 7,000 | >2,000 | 8,000 |
| 23 | >2,000 | 15,000 | >2,000 | 17,000 |
| 24 | >2,000 | 13,000 | >2,000 | 16,000 |
| 25 | >2,000 | 7,000 | >2,000 | 8,400 |
| 26 | 1,700 | 1,300 | 1,800 | 1,600 |
| 27 | 1,900 | 1,600 | 1,900 | 1,600 |
| 28 | >2,000 | 4,200 | >2,000 | 4,700 |
| 29 | >2,000 | 3,700 | >2,000 | 4,400 |
| Number of patients above the normal range | 28 | 28 | 28 | 28 |
| % of patients above the normal range | (97%) | (97%) | (97%) | (97%) |

TABLE IX

Comparison of Non-Specific Binding Using the Reference Boil Assay and the No-Boil Assays of RIA Products, Inc. and Diagnostic Products, Inc. in both their Standard Forms and as Modified to Make them Approach the No-Boil Assay of the Present Invention

| Subject or Patient (#) | Unsaturated $B_{12}$-Binding Ability (pg/ml) | Non-Specific Binding | | | | |
|---|---|---|---|---|---|---|
| | | Corning Reference Boil Assay (%) | RIA Products No-Boil ComboStat Kit | | Diagnostic Products No-Boil Dualcount Kit | |
| | | | Standard (%) | Modified (%) | Standard (%) | Modified (%) |
| Normal | | | | | | |
| 1 | 470 | 2.3 | 1.5 | | — | 0.8 |
| 4 | 360 | 2.4 | 0.8 | | — | 0.8 |
| 6 | 170 | 2.6 | 1.0 | | −1.1 | |
| 12 | 100 | 2.4 | 1.6 | | −1.2 | |
| 20 | 710 | 3.0 | 1.9 | | −0.5 | |
| 21 | 520 | 2.2 | 0.8 | | −1.1 | |
| 30 | 340 | 1.7 | 0.8 | | −1.4 | |
| 36 | 230 | 1.8 | 0.5 | | −0.9 | |
| 39 | 580 | 1.3 | 0.5 | | −1.0 | |
| 40 | 920 | 2.5 | 1.6 | | −0.8 | |
| 41 | 2,400 | 3.2 | 4.2 | | 0.8 | |
| 43 | 560 | 2.8 | 1.2 | | −0.2 | |
| 45 | 920 | 3.1 | 2.2 | | −0.5 | |
| 49 | 160 | 1.7 | 0.3 | | −1.6 | |
| Mean | 603 | 2.4 | 1.3 | −0.8 | | |
| Low $B_{12}$, Antibody Negative | | | | | | |
| 1 | 870 | 2.2 | 0.6 | | 1.5 | |
| 2 | 2,600 | 2.1 | 0.7 | | 0.1 | |
| 3 | 1,300 | 2.2 | 0.6 | | 0.9 | |
| 4 | 2,300 | 1.9 | 0.5 | | −0.7 | |
| 5 | 1,400 | 1.7 | 0.4 | | −0.5 | |
| 6 | 850 | 2.6 | 1.0 | | 0.7 | |
| 7 | 1,800 | 1.7 | 0.4 | | −0.8 | |
| 8 | 1,400 | 1.7 | 0.4 | | −0.4 | |
| 9 | 1,100 | 1.9 | 0.6 | | −0.6 | |
| 10 | 1,200 | 1.5 | 0.0 | | 0.4 | |
| 11 | 900 | 1.5 | 0.3 | | −0.6 | |
| 12 | 1,100 | 3.3 | 1.5 | | 0.1 | |
| Mean | 1,402 | 2.0 | 0.6 | | 0.0 | |
| Chronic Myelogenous Leukemia | | | | | | |
| 1 | 2,400 | 3.9 | 9.7 | 1.1 | 0.6 | 1.6 |
| 2 | 3,200 | 4.5 | 9.3 | 0.9 | 3.6 | 2.0 |
| 3 | 4,500 | 6.3 | 13.3 | 1.7 | 3.5 | 2.0 |
| 4 | 1,200 | 3.9 | 5.9 | 0.7 | 1.0 | 1.4 |
| 5 | 3,900 | 6.0 | 18.5 | 2.2 | 4.4 | 2.3 |
| 6 | 17,000 | 12.4 | 37.0 | 7.8 | 16.3 | 7.2 |
| 7 | 2,000 | 9.1 | 26.2 | 5.6 | 6.4 | 5.3 |

TABLE IX-continued

Comparison of Non-Specific Binding Using the Reference Boil Assay and the No-Boil Assays of RIA Products, Inc. and Diagnostic Products, Inc. in both their Standard Forms and as Modified to Make them Approach the No-Boil Assay of the Present Invention

| Subject or Patient (#) | Unsaturated $B_{12}$-Binding Ability (pg/ml) | Corning Reference Boil Assay (%) | RIA Products No-Boil ComboStat Kit Standard (%) | RIA Products No-Boil ComboStat Kit Modified (%) | Diagnostic Products No-Boil Dualcount Kit Standard (%) | Diagnostic Products No-Boil Dualcount Kit Modified (%) |
|---|---|---|---|---|---|---|
| 8 | 1,800 | 5.3 | 11.1 | 1.4 | 0.6 | 0.9 |
| 9 | 14,000 | 3.1 | 16.3 | 6.2 | 18.1 | 6.1 |
| 10 | 3,500 | 6.7 | 18.0 | 2.2 | 0.9 | 1.2 |
| 11 | 15,000 | 4.0 | 14.8 | 5.9 | 17.4 | 5.6 |
| 12 | 860 | 2.2 | 1.3 | −0.1 | −0.7 | 0.0 |
| 13 | 15,000 | 4.2 | 46.6 | 6.4 | 18.6 | 6.6 |
| 14 | 7,900 | −0.3 | 37.7 | 4.6 | 12.2 | 3.6 |
| 16 | 7,100 | 0.0 | 11.3 | 4.7 | 11.2 | 3.6 |
| 17 | 7,300 | 0.6 | 14.0 | 4.5 | 11.1 | 4.6 |
| 18 | 7,400 | −2.1 | 32.7 | 3.0 | 8.9 | 1.9 |
| Mean | 7,170 | 4.1 | 19.0 | 3.5 | 7.4 | 3.1 |

Table IX also indicates that when the assay material of the kits was "Modified" in the manner indicated in Table XV, to bring the commercial kits into closer agreement with the compositions and procedures of the present invention, then the results for these modified kits came into closer agreement with the Reference assay. However, neither the need for the modifications nor the modifications themselves would have been appreciated or made without the recognition of the problems and the solutions of the present invention.

As shown in Table X, the RIA Products and Diagnostic Products kits were also compared with the Corning Reference assay for the same 50 normal subjects tested by the no-boil assay of the present invention in Table V. It will be seen that both of these commercial kits were in acceptable agreement with the Corning Reference assay in the values obtained for all of the normal subjects and in the normal ranges indicated by these values.

However, when the RIA Products and Diagnostic Products Kits were used to test a number of patients who were vitamin $B_{12}$ deficient, without IF-blocking antibodies, as set forth in Table XI, the RIA Products procedure failed to identify two-thirds of the subjects as being vitamin $B_{12}$ deficient, while the Diagnostics Products kit identified 100% of the vitamin $B_{12}$ deficient subjects Table XI should be compared with Table VI, in which the same tests were reported for the no-boil assay of the present invention, the no-boil assay of the present invention giving 100% accuracy in assay results. As discussed below, the failure of the RIA Products kit to correctly identify many vitamin $B_{12}$ deficient patients without IF-blocking antibodies is believed to be due to the high amount of DTT used in its procedure which subsequently interferes with the ability of IF to bind vitamin $B_{12}$ in the assay itself, such interference being greater with prepared serum samples than in prepared non-serum samples containing known amounts of vitamin $B_{12}$ which are used to construct a standard curve.

Now at this time, as set forth in Table XII, samples which were known to be vitamin $B_{12}$ deficient, and to have IF-blocking antibodies were assayed using both the RIA Products and Diagnostic Products kits and compared with the Corning Reference assay. Table XII should be compared with Table VII which set forth similar tests using the assay of the present invention. A smaller number of samples are used in Table XII than in Table VII due to the fact that many of the samples used in Table VII were depleted and therefore unavailable for further testing.

TABLE X

Comparison of Serum Vitamin $B_{12}$ Values in 50 Normal Subjects Using the Reference Boil Assay and No-Boil Assays of RIA Products, Inc. and Diagnostic Products, Inc.

| Normal Subjects (#) | Corning Reference Boil Assay (pg/ml) | RIA Products No-Boil ComboStat Kit (pg/ml) | Diagnostic Products No-Boil Dualcount Kit (pg/ml) |
|---|---|---|---|
| 1 | 243 | 203 | 347 |
| 2 | 322 | 357 | 406 |
| 3 | 343 | 603 | 750 |
| 4 | 273 | 243 | 275 |
| 5 | 350 | 445 | 412 |
| 6 | 430 | 420 | 493 |
| 7 | 225 | 181 | 175 |
| 8 | 270 | 340 | 283 |
| 9 | 429 | 463 | 420 |
| 10 | 303 | 235 | 283 |
| 11 | 730 | 750 | 725 |
| 12 | 397 | 333 | 315 |
| 13 | 182 | 247 | 220 |
| 14 | 234 | 310 | 310 |
| 15 | 330 | 400 | 426 |
| 16 | 397 | 450 | 470 |
| 17 | 455 | 455 | 520 |
| 18 | 181 | 204 | 177 |
| 19 | 363 | 410 | 426 |
| 20 | 360 | 400 | 467 |
| 21 | 175 | 220 | 234 |
| 22 | 220 | 303 | 285 |
| 23 | 540 | 645 | 587 |
| 24 | 345 | 377 | 446 |
| 25 | 338 | 480 | 460 |
| 26 | 303 | 417 | 340 |
| 27 | 385 | 240 | 460 |
| 28 | 400 | 525 | 480 |
| 29 | 360 | 545 | 450 |
| 30 | 580 | 660 | 690 |
| 31 | 197 | 290 | 287 |
| 32 | 795 | 860 | 860 |
| 33 | 380 | 527 | 555 |
| 34 | 442 | 395 | 575 |
| 35 | 465 | 480 | 570 |
| 36 | 232 | 350 | 283 |
| 37 | 308 | 410 | 450 |
| 38 | 250 | 397 | 420 |
| 39 | 193 | 350 | 357 |
| 40 | 322 | 366 | 553 |
| 41 | 385 | 565 | 565 |
| 42 | 162 | 194 | 347 |

TABLE X-continued

Comparison of Serum Vitamin $B_{12}$ Values in 50 Normal Subjects Using the Reference Boil Assay and No-Boil Assays of RIA Products, Inc. and Diagnostic Products, Inc.

| | Serum Vitamin $B_{12}$ Values | | |
|---|---|---|---|
| Normal Subjects (#) | Corning Reference Boil Assay (pg/ml) | RIA Products No-Boil ComboStat Kit (pg/ml) | Diagnostic Products No-Boil Dualcount Kit (pg/ml) |
| 43 | 215 | 360 | 365 |
| 44 | 352 | 645 | 585 |
| 45 | 700 | 800 | 1,060 |
| 46 | 218 | 240 | 375 |
| 47 | 377 | 345 | 545 |
| 48 | 233 | 312 | 310 |
| 49 | 450 | 780 | 535 |
| 50 | 150 | 200 | 177 |
| Mean | 346 | 415 | 442 |
| Normal Range[a] | 148–696 | 172–853 | 187–901 |

[a]Mean ± 2 standard deviations after log normalization to correct for skewness of the data to higher values.

TABLE XI

Comparison of Serum Vitamin $B_{12}$ Values in 12 Patients Without Anti-IF Blocking Antibodies Using the Reference Boil Assay and the No-Boil Assays of RIA Products, Inc. and Diagnostic Products, Inc.

| | Serum Vitamin $B_{12}$ Values | | |
|---|---|---|---|
| Low $B_{12}$, Antibody Negative Patients (#) | Corning Reference Boil Assay (pg/ml) | RIA Products No Boil ComboStat Kit (pg/ml) | Diagnostic Products No-Boil Dualcount Kit (pg/ml) |
| 1 | 18 | 110 | 36 |
| 2 | 128 | 224 | 145 |
| 3 | 108 | 175 | 54 |
| 4 | 120 | 235 | 140 |
| 5 | 5 | 117 | 29 |
| 6 | 92 | 224 | 107 |
| 7 | 77 | 177 | 61 |
| 8 | 78 | 170 | 119 |
| 9 | 107 | 183 | 128 |
| 10 | 117 | 240 | 175 |
| 11 | 80 | 155 | 138 |
| 12 | 88 | 185 | 146 |
| Mean | 85 | 183 | 106 |
| Number of patients below the normal range | (12) | (4) | (12) |
| % of patients below the normal range | (100%) | (33%) | (100%) |

TABLE XII

Comparison of Serum Vitamin $B_{12}$ Values in 12 Patients with Anti-IF Blocking Antibodies Using the Reference Boil Assay and the No-Boil Assays of RIA Products, Inc. and Diagnostic Products, Inc.

| | Serum Vitamin $B_{12}$ Values | | |
|---|---|---|---|
| Low $B_{12}$, Antibody Positive Patients (#) | Corning Reference Boil Assay (pg/ml) | RIA Products No-Boil ComboStat Kit (pg/ml) | No-Boil Assay Diagnostic Products No-Boil Dualcount Kit (pg/ml) |
| 3 | 110 | 245 | 195 |
| 13 | 30 | 140 | 96 |
| 15 | 15 | 180 | 38 |
| 16 | 83 | 470 | 168 |
| 18 | 0 | 150 | 31 |
| 32 | 91 | 250 | 136 |
| 34 | 72 | 125 | 113 |
| 45 | 122 | 185 | 155 |
| 46 | 142 | 205 | 191 |
| 52 | 18 | 107 | 43 |
| 59 | 31 | 110 | 58 |
| 64 | 90 | 295 | 57 |
| 83 | 39 | 200 | 17 |
| Mean | 67 | 222 | 107 |
| Number of patients below the normal range | (12) | (5) | (10) |
| % of patients below the normal range | (100%) | (42%) | (83%) |

However, even in this abbreviated comparison of 12 vitamin $B_{12}$ deficient subjects with IF-blocking antibodies, the RIA Products kit identified less than 50% of the deficient subjects as being deficient and the Diagnostic Products kit identified only 10 to 12 (83%) as being vitamin $B_{12}$ deficient. That the RIA Products kit is particularly inaccurate with some vitamin $B_{12}$ deficient patient samples with IF-blocking antibodies is supported by the value of 470 pg/ml as set forth for patient #16 in Table XII, since this value is higher than the mean value of 415 pg/ml that was obtained for the 50 normal subjects using the RIA Products kit as set forth in Table X. Both of these commercial kits provide results which are not only inaccurate, but also totally clinically unacceptable as to patient diagnosis and treatment. By comparison, referring to Table VII, the no-boil assay of the present invention is clinically acceptable as to patient diagnosis and treatment, in that it identified 100% of the vitamin $B_{12}$ deficient subjects. The fact that Table VII tested 111, instead of only 12 IF-blocking antibody positive subjects, makes the proven accuracy and precision of the no-boil assay of the present invention even more evident.

As in Table VIII using the present invention, subjects with CML are reported in Tables XIII and XIV, using the RIA Products and Diagnostic Products kits. Again, Tables XIII and XIV are somewhat abbreviated due to the depletion and unavailability of some samples. The central columns in Tables XIII and XIV, marked above and below with an * set forth the results which would be obtained using the commercial kits as they are intended to be used. It is noted that when so used the RIA Products kit identified only 6 of 17 samples as being high in vitamin $B_{12}$, and that the Diagnostic Products kit identified only 10 of 17 samples as being high in vitamin $B_{12}$. Therefore, these commercial tests would be unreliable in identifying subjects with high vitamin $B_{12}$, as a tool in diagnosing CML. By comparison, as set forth in Table VIII, the no-boil assay of the present invention identifies 100% of the CML patients with high vitamin $B_{12}$ levels as being high.

TABLE XIII

Comparison of Serum Vitamin $B_{12}$ Values in 18 Patients with Chronic Myelogenous Leukemia Using the Reference Boil Assay, and the No-Boil Assay of RIA Products, Inc. in both Standard Form and as Modified to Make it Approach the No-Boil Assay of the Present Invention

| Chronic Myelogenous Leukemia Patients (#) | Corning Reference Boil Assay Volume Assayed | | RIA Products * No-Boil ComboStat Kit | | | |
|---|---|---|---|---|---|---|
| | | | Standard Assay Volume Assayed | | Modified Assay Volume Assayed | |
| | Standard (pg/ml) | Diluted (pg/ml) | Standard (pg/ml) | Diluted (pg/ml) | Standard (pg/ml) | Diluted (pg/ml) |
| 1 | >2,000 | 4,100 | 1,000 | 4,300 | >2,000 | 4,500 |
| 2 | >2,000 | 3,500 | 1,000 | 2,700 | >2,000 | 3,200 |
| 3 | >2,000 | 2,300 | 720 | 2,100 | 1,700 | 1,700 |
| 4 | >2,000 | 3,300 | 1,400 | 3,100 | >2,000 | 3,500 |
| 5 | >2,000 | 4,400 | 890 | 4,200 | >2,000 | 5,300 |
| 6 | >2,000 | 7,500 | 300 | 7,000 | 1,700 | 8,600 |
| 7 | >2,000 | 14,000 | 580 | 15,000 | >2,000 | 18,000 |
| 8 | >2,000 | 4,700 | 1,400 | 4,300 | >2,000 | 4,400 |
| 9 | >2,000 | 6,300 | 290 | 6,000 | >2,000 | 7,000 |
| 10 | >2,000 | 5,000 | 990 | 5,800 | >2,000 | 6,700 |
| 11 | >2,000 | 6,300 | 310 | 6,600 | >2,000 | 7,300 |
| 12 | 460 | 500 | 550 | 580 | 500 | 570 |
| 13 | >2,000 | 6,800 | 320 | 6,000 | 2,000 | 7,300 |
| 14 | >2,000 | 6,300 | 460 | 6,600 | >2,000 | 7,500 |
| 15 | >2,000 | 5,800 | 310 | 5,000 | >2,000 | 6,200 |
| 16 | >2,000 | 6,600 | 500 | 7,200 | >2,000 | 7,500 |
| 17 | >2,000 | 8,500 | 510 | 8,600 | >2,000 | 9,800 |
| 18 | >2,000 | 4,900 | 540 | 5,100 | >2,000 | 5,800 |
| Number of patients above the normal range | (17) | (17) | (6) | (17) | (17) | (17) |
| % of patients above the normal range | (94%) | (94%) | (33%) * | (94%) | (94%) | (94%) |

TABLE XIV

Comparison of Serum Vitamin $B_{12}$ Values in 18 Patients with Chronic Myelogenous Leukemia Using the Reference Boil Assay, and the No-Boil Assay of Diagnostic Products in both Standard Form and as Modified to make it Approach the No-Boil Assay of the Present Invention

| Chronic Myelogenous Leukemia Patients (#) | Corning Reference Boil Assay Volume Assayed | | Diagnostic Products * No-Boil Dualcount Kit | | | |
|---|---|---|---|---|---|---|
| | | | Standard Assay Volume Assayed | | Modified Assay Volume Assayed | |
| | Standard (pg/ml) | Diluted (pg/ml) | Standard (pg/ml) | Diluted (pg/ml) | Standard (pg/ml) | Diluted (pg/ml) |
| 1 | >2,000 | 4,100 | 1,700 | 4,700 | >2,000 | 4,400 |
| 2 | >2,000 | 3,500 | 1,400 | 3,000 | >2,000 | 2,400 |
| 3 | >2,000 | 2,300 | 890 | 1,900 | 1,800 | 1,700 |
| 4 | >2,000 | 3,300 | 1,700 | 2,800 | >2,000 | 2,100 |
| 5 | >2,000 | 4,400 | 1,200 | 4,400 | >2,000 | 4,700 |
| 6 | >2,000 | 7,500 | 500 | 6,500 | >2,000 | 8,200 |
| 7 | >2,000 | 14,000 | 1,400 | 17,000 | >2,000 | 21,000 |
| 8 | >2,000 | 4,700 | 1,800 | 5,200 | >2,000 | 4,100 |
| 9 | >2,000 | 6,300 | 680 | 6,600 | >2,000 | 7,300 |
| 10 | >2,000 | 5,000 | 1,700 | 5,900 | >2,000 | 6,700 |
| 11 | >2,000 | 6,300 | 640 | 5,900 | >2,000 | 7,500 |
| 12 | 460 | 500 | 480 | 510 | 520 | 400 |
| 13 | >2,000 | 6,800 | 600 | 6,600 | >2,000 | 7,400 |
| 14 | >2,000 | 6,300 | 990 | 6,900 | >2,000 | 8,600 |
| 15 | >2,000 | 5,800 | 640 | 5,500 | >2,000 | 6,100 |
| 16 | >2,000 | 6,600 | 900 | 7,000 | >2,000 | 8,400 |
| 17 | >2,000 | 8,500 | 990 | 9,900 | >2,000 | 11,000 |
| 18 | >2,000 | 4,900 | 1,100 | 5,400 | >2,000 | 5,400 |
| Number of patients above the normal range | (17) | (17) | (10) | (17) | (17) | (17) |
| % of patients above the normal range | (94%) | (94%) | (56%) | (94%) | (94%) | (94%) |

Again, referring to Tables XIII and XIV, when the RIA Products kit and Diagnostic Products Kit were each varied, first by dilution, and then by modifications as set forth in Table XV, and then by both modification and dilution, the kits both gave completely accurate ther of which reactions will result in erroneous sample vitamin $B_{12}$ readings.

TABLE XV

Conditions of No-Boil Assays in Standard Form and Those Modified in Accord with the Present Invention

| | Conditions during Extraction | | | | | | Incubation Time During Extraction (Min) | |
|---|---|---|---|---|---|---|---|---|
| | Serum Sample Volume, μl | 100 ng Cobinamide | NaOH | DTT | Dilution of Serum | μl after Dilution | After DTT | After NaOH |
| No-Boil Assay of the Present Invention | 200 | + | 0.33M | 0.043M | 0.67 | 300 | 0 | 20 |
| RIA Products No-Boil ComboStat Kit | | | | | | | | |
| Standard | 200 | − | 0.20M[b] | 0.052M[c] | 0.40[d] | 500 | 15 | 5 |
| Modified[a] | 200 | + | 0.25M | 0.065M | 0.50 | 400 | 0 | 20 |
| Diagnostic Products No-Boil Dualcount Kit | | | | | | | | |
| Standard | 200 | − | 0.27[b] | 0.017M[d] | 0.27[d] | 750 | 30 | 15 |
| Modified[a] | 200 | + | 0.44 | 0.029M | 0.44 | 450 | 0 | 15 |

[a]Modifications were made with the individual kit reagents to approach as closely as possible the method of the present invention, subject to the constraints imposed by the manufacturers' reagents.
[b]Based on measurements obtained by Titration with HCl.
[c]Based on information obtained from RIA Products, Inc.
[d]Calculated from information supplied in the package labels.

results in identifying the CML patients with high vitamin $B_{12}$. However, in the absence of the teaching of the present invention, one would not know to modify the RIA Products or Diagnostic Products kits in this manner.

Reference is now made to Table XV. This table sets forth the assay preparation conditions for preferred embodiments of the present invention as well as the standard assay preparation conditions for the RIA Products no-boil kit and the Diagnostic Products no-boil kit. It also sets forth data indicative of the types of modifications which were made in each of these kits as discussed in Tables IX, XIII and XIV. Table XV also allows ease of comparison between the preferred embodiments of the present invention and the standard embodiments of the RIA Products and Diagnostic Products kits. It is immediately apparent that each of the no-boil tests utilizes the same initial volume of serum sample. The initial volume of sample is not critical, and is a matter of choice, but of course, all other procedures and ingredients must be adjusted to accomodate the volume of sample utilized. It is next noted that the standard RIA Products and Diagnostic Products procedures do not utilize a vitamin $B_{12}$ analogue in the assay preparation, while the preferred embodiments of the present invention utilize cobinamide analogue. It is next noted that each of the procedures utilizes the strong base NaOH, but that the concentration of the base in the preferred embodiments of the present invention is about 22% to about 65% greater than the concentration of base in the RIA Products kit and the Diagnostic Products kit, respectively. It is theorized that the concentration of the base is an important factor, in combination with the other ingredients and their concentrations, in providing the most complete release of endogenous vitamin $B_{12}$ from endogenous binding protein, and in the initial inactivation or destruction of both endogenous binding protein and IF-blocking antibodies. One of the several theories of the present invention is that no-boil assay preparation does not substantially completely destroy or inhibit endogenous binding protein which is released from sample endogenous vitamin $B_{12}$ or which is otherwise present in the serum sample, thus allowing the undestroyed or uninhibited endogenous binding protein to recombine with the sample endogenous vitamin $B_{12}$ and/or the added radioactive vitamin $B_{12}$, ei- Therefore, the addition of an analogue which is capable of binding substantially all endogenous binding protein, whether released from vitamin $B_{12}$ or otherwise present in the sample, was theorized and provided a serum assay preparation process and composition which would provide more accurate assays. Cobinamide is the vitamin $B_{12}$ analogue of choice due to its ease of availability and low cost. However, any other vitamin $B_{12}$ analogue which is capable of binding with endogenous binding protein, and which will not inhibit or interfere with the intrinsic factor utilized as the binder in the assay is of substantial importance in the procedures and compositions of the present invention.

Each of the procedures utilizes potassium cyanide, not shown in Table XV. The presence of cyanide in the preparation for assay has long been a standard procedure in order to convert the vitamin $B_{12}$ being tested to its most stable form, cyanocobalamin. As has previously been noted, Ithakissios, et. al. has indicated that the combination of a strong base with cyanide provides excellent vitamin $B_{12}$ release. The present invention has verified that the combination of cyanide and a strong base by themselves do not provide optimum vitamin $B_{12}$ release, as set forth in Table I, for which all of the procedures used cyanide, and as set forth in Tables IX, XIII and XIV for the RIA Products and Diagnostic Products kits, both of which use a strong base and cyanide. It has thereby been verified that this combination is apparently not as useful in releasing substantially all vitamin $B_{12}$ as has been reported.

Each of the procedures utilize DTT in the extraction procedure. It is first noted that both the RIA Products and Diagnostic Products kits are intended for the simultaneous determination of both vitamin $B_{12}$ and folate, and that it is well known in the art to utilize a sulfhydral compound such as DTT to stabilize the folate. However, in the present invention, the sulfhydral compound is utilized primarily for its known ability as a disulfide protein destroying compound, a previously unappreciated or unrecognized use. As such, it has been theorized that it has utility in both releasing endogeneous vitamin $B_{12}$ from endogenous binding protein and in substantially destroying both endogenous binding protein and IF-blocking antibodies which are, or may be, present in the sample undergoing assay. As demonstrated in Table III, and the discussion related thereto, the selection of the type and the amount of protein destroying compound may be critical in those samples which contain IF-blocking antibodies which are resistant to destruction. It is noted that the concentration of DTT utilized in the preferred embodiments of the present invention lies intermediately between the concentration of DTT utilized in the RIA Products kit and the amount utilized the Diagnostic Products kit. However, it is further noted that as set forth in the Tables, both the RIA Products and the Diagnostic Products kits failed to identify a substantial number of low vitamin $B_{12}$ samples containing IF-blocking antibodies and a substantial number of high vitamin $B_{12}$ CML samples. It is further noted that the RIA Products kit, which contains the greatest amount of DTT, gave the worst results for the analysis of vitamin $B_{12}$ in CML patients. It is also further noted that the RIA Products kit failed to identify a substantial number of low vitamin $B_{12}$ samples without IF-blocking antibodies. It is theorized that the high concentration of DTT may have provided the additional margin of error in the CML analyses and/or in low vitamin $B_{12}$ without IF-blocking antibody analyses. Therefore, it is difficult at this time, with scientific certainty, to indicate the specific concentration of sulfhydral compound which should be utilized in the preparation of samples for vitamin $B_{12}$ assay. It would appear, that the relationship between the sulfhydral compound and the amounts and types of other ingredients is of importance in providing an optimum no-boil test procedure. It is, of course, noted that the —SH moiety of the sulfhydral compounds is what supplies the disulfide protein destroying capability, and that a compound such as DTT has twice an many —SH moieties as a compound such as BME. Therefore, the selection of the sulfhydral compound for use in combination with the other ingredients of the present invention should consider both the —SH concentration and structure.

It is also theorized that the cobinamide aids in the release of endogenous vitamin $B_{12}$ from endogenous binding protein. This is supported by the data in Table I which indicate that the greatest amount of vitamin $B_{12}$ release occurred in those samples which included cobinamide (Cbi) in the assay preparation composition. Therefore, the cobinamide has utility not only to bind endogenous binding protein in the sample, but also to aid in the release of vitamin $B_{12}$ in the sample. In hindsight, it may be theorized that the analogue acts to displace vitamin $B_{12}$ from the endogenous binding protein, thus diluting the concentration of endogenous binding protein-vitamin $B_{12}$ complex in the solution and driving the reaction which releases endogenous binding protein from vitamin $B_{12}$ in the direction of additional release.

It is also of interest to note that both the RIA Products and the Diagnostic Products kits allow substantial incubation time, at room temperature, before the strong base is added to the serum undergoing assay preparation, while the preferred embodiments of the present invention add the strong base simultaneously or with other assay preparation ingredients. It is theorized that since it is now recognized that there is a need to destroy or inhibit substantially all endogenous binding protein in the sample and prevent it from recombining with vitamin $B_{12}$ or combining with radioactive vitamin $B_{12}$, and as a strong base is a good protein destroying material, that the simultaneous or early addition of the strong base inhibits the recombination of endogenous binding protein with vitamin $B_{12}$ and inhibits the combining of endogenous binding protein with radioactive vitamin $B_{12}$ to maintain the amount of released vitamin $B_{12}$ of both kinds at optimum levels.

Based on the experimental results achieved by the preferred embodiments of the present invention and the comparative results achieved by out original prototype procedure and by the RIA Products and Diagnostic Products kits, it appears, and is theorized, that the concentration of the solutions (or volume) at the time of extraction, the nature and amounts of the ingredients, and the various incubation times, may all be of some importance in situations where samples containing IF-blocking antibodies or CML patient samples are being analyzed. Analysis of the data obtained with the RIA Products kit for the vitamin $B_{12}$ deficient patient samples without IF-blocking antibodies indicates that this may also be true at the time of the actual assay. These finding verify the importance of using samples from vitamin $B_{12}$ deficient patients, both with and without IF-blocking antibodies, and from CML patients, in selecting individual ingredients, and their combinations and amounts and concentrations and various incubation times, in both the preparation and assay procedures used in vitamin $B_{12}$ determinations. The importance of using more than one, and more than just a few patient samples from each of the individual patient groups to verify the assay has also been shown since the use of only some of the patient samples as set forth in Tables II, IX, XI, XII, XIII and XIV would have indicated that our original prototype procedure and the current procedures of the RIA Products and Diagnostic Products kits were acceptable both scientifically and clinically, whereas the use of additional and other patient samples as set forth in the same tables clearly establishes that none of these procedures is acceptable, either scientifically or clinically.

Finally, reference to Table XV indicates what modifications were made to the standard RIA Products kit and the standard Diagnostic Products kit, in terms of the addition of a vitamin $B_{12}$ analogue, cobinamide, the adjustment of the concentrations of the strong base, NaOH and sulfhydral compound (DTT) and the volume and therefore the concentration of the test solutions and procedures. Reference to Tables IX, XIII and XIV indicates that utilizing these modifications, the commercially available kits now provided improved conditions, of the type achieved by the preferred embodiments of the present invention. The kits could not be modified with complete accuracy or certainty to match the preferred embodiments of the present invention, since their initial ingredients presented some constraints and since further, their actual contents were not known with complete certainty. Nevertheless, the modifications made did improve the kits and bring them to clinically acceptable levels.

The term "clinically acceptable" as utilized herein, is intended to mean substantially 100% accuracy. For example, referring again to Table III in which Sample #17 was missed, apparently due to the presence of difficultly destroyed IF-blocking antibodies, this inaccuracy could have resulted in failure to diagnose that patient's vitamin $B_{12}$ deficiency. Failure to identify and treat that deficiency could have resulted in the development of potentially fatal blood and/or neurologic abnormalities. Neurological abnormalities, once developed, may be quite serious, as they are not always subject to reversal by subsequent treatment with vitamin $B_{12}$.

Referring to Table XVI, a comparison between the standard curves utilized for the Corning reference boil assay, the RIA Products no-boil assay, the Diagnostic Products no-boil assay, with the no-boil assay of the present invention is made. These standard curves are indicative of the number of radioactive counts bound to intrinsic factor which in turn correspond with the amount of non-radioactive vitamin $B_{12}$, in the known samples, in pg/ml. Initially, it is noted that the standard curves for the Corning reference assay, and the no-boil assay of the present invention are substantially indistinguishable from one another. While the standard curves for the RIA Products kit and the Diagnostic Products kit do vary from the Corning assay, as long as they are reproducible for those kits, this variation represents no problem. However, in any of the four assays set forth in Table XVI, a false variation, i.e. one not related to the amount of vitamin $B_{12}$ in the sample to-be-tested, of as little as 10% can result in a major variation in the amount of non-radioactive vitamin $B_{12}$ which is determined to be present in a to-be-tested sample. Now, based upon the teaching and analysis of the present invention, it is seen that false variations of as much as 46% of bound radioactive vitamin $B_{12}$ are possible utilizing the RIA Products and Diagnostic Products kits, due to their apparent failure to completely release all bound vitamin $B_{12}$, and/or completely substantially inhibit or destroy all endogenous binding protein, and/or completely inhibit or destroy all IF-blocking antibodies and/or bind undestroyed or uninhibited endogenous binding protein.

In preferred embodiments of the present invention, after the samples were prepared for assay, they were neutralized and allowed to incubate with soluble IF, followed by the addition of albumin coated charcoal to adsorb the unbound sample vitamin $B_{12}$ and radioactive vitamin $B_{12}$. In a modification of the present invention, after the sample is prepared for assay, and neutralized, rather than adding the IF binder to the solution as a soluble ingredient, another method of adding IF to the system can be utilized, and is actually preferred as giving more reliable assay results. The form of IF which was used, was an article consisting of small glass beads to which IF is covalently attached. Such IF-glass beads were made available on an experimental basis from Corning. When utilizing such IF-glass beads, the final steps of the assay procedure vary from the procedures previously described. Previously, albumin coated charcoal was added to the liquid to adsorb the unbound vitamin $B_{12}$, both sample and radioactive, and the supernatant liquid, containing sample and radioactive vitamin $B_{12}$ bound to IF, was subjected to analysis for radioactive counts. Now, utilizing IF-glass beads, the sample and radioactive $B_{12}$ becomes bound to the IF on the glass beads. Because the glass beads have a much greater density than the liquid composition to which they are added, they are easily centrifuged to the bottom of the tube. Then, subsequent removal of the supernatant liquid leaves one with the natural and radioactive vitamin $B_{12}$ bound to the IF on the glass beads. Then, the easily separated and handled glass beads are subjected to radioactive count in order to determine the amount of natural vitamin $B_{12}$ in the sample. For the sake of accuracy, it is noted that all data concerning the present invention which are set forth in Tables IV–XVI for the preferred embodiments of the present invention were gathered utilizing IF-glass beads rather than by the addition of soluble IF to the solution followed by the removal of unbound vitamin $B_{12}$ utilizing charcoal. For at least two reasons relevant to the present invention, it is believed that the use of IF-glass beads in the completion of the assay provides more accurate assay results than the free IF and charcoal technique.

One reason is that IF-blocking antibodies do not bind as well to IF-glass beads as they do to soluble IF. A second reason is that non-specific binding to endogenous binding protein is present in the supernatant with unbound vitamin $B_{12}$ in the IF-glass assay and thus can not lead to a falsely low reading of sample vitamin $B_{12}$ as can occur with the soluble IF and charcoal assay where non-specific binding to endogenous binding protein is present in the supernatant fraction together with vitamin $B_{12}$ bound to IF and thereby can lead to a falsely low reading of sample vitamin $B_{12}$.

TABLE XVI

Standard Curves Obtained with the Reference Boil Assay, the No-Boil Assay of the Present Invention, and the No-Boil Assays of RIA Products, Inc. and Diagnostic Products, Inc.

| | % Binding of [$^{57}$Co]Vitamin $B_{12}$ Observed | | | |
|---|---|---|---|---|
| Non-radioactive Vitamin $B_{12}$ Added (pg) | Corning Reference Boil Assay (%) | No-Boil Assay of-the Present Invention (%) | RIA Products No-Boil ComboStat Kit (%) | Diagnostic Products No-Boil Dualcount (%) |
| 0 | (100) | (100) | (100) | (100) |
| 50 | — | — | 94 | 88 |
| 100 | 86 | 83 | — | 79 |
| 150 | — | — | 81 | — |
| 250 | 78 | 76 | — | — |
| 300 | — | — | — | 57 |
| 400 | — | — | 52 | — |
| 500 | 61 | 61 | — | — |
| 600 | — | — | — | 37 |
| 1,000 | 45 | 45 | 26 | — |
| 1,200 | — | — | — | 22 |
| 2,000 | 29 | 30 | 14 | — |
| 2,400 | — | — | — | 11 |

Of course, IF bound to solid non-interferring material other than glass for use in completion of the assay would have similar improved properties in carrying out the assay.

As shown with regard to a modification of the preferred embodiments and in the discussion of Table I and Table II, much of the initial work for the present invention was carried out in a manner which allowed for the simultaneous analysis of folate along with the analysis for vitamin $B_{12}$. It is more specifically noted that the no-boil release procedure and composition of the present invention are also useful for the no-boil release of folate for testing in serum. As noted in Table XVII, the simultaneously RID assay of both vitamin $B_{12}$ and folate is capable of utilizing the teaching of the present invention. It would appear that when folate alone is being assayed, that the vitamin $B_{12}$ analogue may not be needed in the procedure and composition, although it can be present if this makes the preparation of common reagents for vitamin $B_{12}$ and folate assays more convenient.

The data utilized in analyzing and perfecting the present invention is of great value in showing the need for proper scientific and clinical procedures in determining the accuracy of an assay. If only normals had been tested for vitamin $B_{12}$, or if only low vitamin $B_{12}$ samples without IF-blocking antibodies had been tested, or if only a small number of samples low in vitamin $B_{12}$ and including IF-blocking antibodies had been tested, or if no CML patients had been tested or insufficient numbers of any of these groups to determine the utility and limits of the prototype procedure and composition had been tested, the results could have resulted in assay procedures and compositions which were ineffective in detecting low vitamin $B_{12}$ samples with and/or without difficult to destroy IF-blocking antibodies and/or abnormally high vitamin $B_{12}$ samples containing high amounts of endogenous binding protein. This could have resulted in faulty assays of the type which were found to exist for the RIA Products and Diagnostic Products commercial kits. It is believed, that for the first time, the present invention has recognized the fact that each sample's IF-blocking antibodies may be unique, and in some instances that the IF-blocking antibodies may be sufficiently difficult to destroy that they may lead to inaccurate assays in some samples. Only the large number of samples ultimately studied in the present invention, as set forth in Table V, could have led to the perfection of an analysis which is accurate regardless of the presence or absence of IF-blocking antibodies, and regardless of the difficulty with which the IF-blocking antibodies are destroyed.

TABLE XVII

Simultaneous Assay of Vitamin $B_{12}$ and Folate using the Corning Reference Boil Assay and the No-Boil Assay of the Present Invention.

| | Serum Vitamin $B_{12}$ | | Serum Folate | |
|---|---|---|---|---|
| Serum Sample | Corning Reference Boil Assay (pg/ml) | No-Boil Assay of the Present Invention (pg/ml) | Corning Reference Boil Assay (ng/ml) | No-Boil Assay of the Present Invention (ng/ml) |
| A | 350 | 360 | 4.2 | 4.0 |
| B | 350 | 330 | 6.2 | 6.4 |
| C | 155 | 165 | 6.4 | 6.6 |
| D | 340 | 340 | 8.3 | 8.9 |
| E | 450 | 470 | 15.0 | 18.5 |
| F | 86 | 5 | 10.0 | 8.5 |
| G | 5 | 5 | 6.8 | 5.5 |
| H | 96 | 65 | 37.5 | 33.5 |
| I | 86 | 82 | 6.2 | 5.1 |
| J | 0 | 0 | 10.3 | 8.0 |

In conclusion it is seen that the objectives of the present invention have been achieved. The present invention discloses and teaches methods for the preparation of mammalian blood, tissue and serum for assay of vitamin $B_{12}$ and of folate, and of both vitamin $B_{12}$ and folate without the need to heat or boil the samples as a step in their preparation for assay. In achieving these objects, optimum procedures and compositions for the release of vitamin $B_{12}$ and folate from a to-be-assayed sample were determined. Additionally, the recognition of problems in vitamin $B_{12}$ RID no-heat methods caused by the presence of endogenous binding protein, and procedures and compositions for substantially destroying or inactivating such endogenous binding protein were developed. Also, procedures and compositions for binding any undestroyed or uninhibited endogenous binding protein, utilizing endogenous binding protein binding vitamin $B_{12}$ analogues were developed. Finally, the recognition of the problem that there are antibodies naturally present in some samples which react with or block intrinsic factor protein was made, and procedures and compositions for substantially inhibiting or destroying such IF-blocking antibodies were made. The procedures and compositions are convenient to use, require less steps than the boiling assay techniques and are time-saving. Additionally, as detailed throughout the present application the preferred embodiments of the present invention are highly accurate, and in some instances actually superior to the Reference boil assay.

Certain preferred compositions have been detailed in the present application, and other combinations and concentrations have been taught. It is noted that the basic combination of ingredients, that is a combination of at least two protein destroying compositions, with or without a vitamin $B_{12}$ analogue to bind the endogenous protein, utilized in the various procedures of the present invention are useful in obtaining the results desired. In preferred embodiments, the amount of endogenous binding protein binding vitamin $B_{12}$ analogue should be sufficient to completely bind the greatest amount of endogenous binding protein capability found in any sample, as for example, CML sample #6 in Tables IV and IX. Of course, to allow for margins of error, ten to one hundred times or more vitamin $B_{12}$ analogue could be utilized with the teaching of the present invention. In a similar manner, the greatest amount of, and the most resistant, IF-blocking antibodies determined should be provided for in the compositions and the procedures of the present invention.

As used herein, the term "heating" is intended to mean the action of actively adding energy to a substance to increase its temperature, but does not include changes in temperature due to contact with an ambient environment. "Boiling" and "boil" are used herein in their ordinary sense, so long as they are caused by the active addition of energy. "Without heating", is the absence of the active addition of energy to a substance. "No-boil" and "without boiling" mean that a substance has not been actively caused to boil. While the compositions and procedures of the present invention are specifically novel in that they require no heating or boiling in the preparation of samples for vitamin $B_{12}$ and/or folate assay, they may be used for heating or boiling and still remain within the teaching of the present invention.

While it is noted that certain preferred embodiments have been set forth, the non-preferred embodiments also have utility in those situations in which there is neither IF-blocking antibodies or substantial amounts of endogenous binding protein. It is also noted that the compositions of the present invention are readily amenable to being placed into convenient kit form and provided to users for use in accordance with the procedures of the present invention.

While the invention has been particularly shown and described with reference to preferred embodiments thereof, it will be understood by those skilled in the art, that the foregoing and other modifications or changes in form and details may be made therein without departing from the spirit and scope of the invention.

What is claimed is:

1. A composition for use in the preparation of a clinical sample for the determination of vitamin $B_{12}$ or folate by competitive binding assay which comprises:
   (A) a material in an amount sufficient to bind with endogenous vitamin $B_{12}$ binding protein present in said clinical sample, said material comprising a vitamin $B_{12}$ analog which does not bind with intrinsic factor nor interfere with the ability of intrinsic factor to bind with vitamin $B_{12}$, said analog being selected from the group cobinamide, CN—Cbl—(Cbde—OH), and (3,5,6 $Me_3$ BZA) (CN, OH) Cba; and (B) at least two components which are capable of destroying and/or inhibiting endogenous binding protein and intrinsic factor antibodies; said material and said components being present in a combined amount sufficient to release all bound vitamin $B_{12}$ from endogenous binding protein, and said endogenous binding protein component and intrinsic factor antibody blocking component are present in a combined amount sufficient to destroy and/or inhibit substantially all endogenous binding protein and intrinsic factor blocking antibodies present in the clinical sample.

2. The method of preparing a mammalian blood tissue or serum sample for vitamin $B_{12}$ or folate assay comprising:
   (A) disassociating and freeing substantially all vitamin $B_{12}$ or folate from endogenous binding protein in said sample without heating or boiling;
   (B) denaturing and destroying substantially all endogenous binding protein in said sample which is free to bind with vitamin $B_{12}$ or folate freed in step A;
   (C) inhibiting and/or blocking substantially all undestroyed endogenous binding protein; and
   (D) inhibiting and/or destroying substantially all intrinsic factor blocking antibodies which are present in the sample.

3. The composition of claim 1 wherein the analog is present at a concentration of about 1 to 10,000 ng per 200 ul of the clinical sample.

4. The composition of claim 1 in which one of the components is a strong base.

5. The composition of claim 4 in which the base is selected from the group consisting of sodium hydroxide, potassium hydroxide, and lithium hydroxide, said base further having a concentration of about 0.02 N to about 4.0 N.

6. The composition of claim 1 in which one of the components is a disulfide protein-destroying compound.

7. The composition of claim 6 in which the disulfide protein-destroying compound is a sulfhydral compound.

8. The composition of claim 7 in which the sulfhydral compound is selected from the group consisting of betamercaptoethanol, thioglycolate, thioglycerol and dithiothreitol.

9. The composition of claim 7 in which the sulfhydral compound is present at a concentration in the range of about 0.004 N to about 0.4 N.

10. The composition of claim 4 in which a sulfhydral compound and a strong base are at least two of the components included to destroy and/or inhibit endogenous binding protein and intrinsic factor blocking antibodies.

11. The composition of claim 10 which comprises cobinamide, dithiothreitol, and sodium hydroxide in an amount sufficient to release substantially all sample vitamin $B_{12}$ from endogenous binding protein, the amount of dithiothreitol and sodium hydroxide are present in a combined amount sufficient to destroy or inhibit substantially all endogenous binding protein and intrinsic factor blocking antibodies, and the amount of cobinamide is sufficient to bind with substantially all undestroyed or uninhibited endogenous binding protein.

12. The composition of claim 4 which also comprises a radioactive labeled vitamin $B_{12}$.

13. The composition of claim 6 which also comprises a radioactive labeled vitamin $B_{12}$.

14. The method of preparing mammalian blood, tissue or serum sample for vitamin $B_{12}$ or folate assay comprising: treating said sample with at least two components to destroy or inhibit substantially all endogenous binding protein, and substantially all intrinsic factor blocking antibodies; and treating said sample with a material to bind endogenous binding protein.

15. The method of claim 14 which further comprises: incubating the treated sample at room temperature; and adding intrinsic factor to the sample after incubation.

16. The method of claim 15 wherein the intrinsic factor is insolubly bound to a solid, inert carrier.

17. The method of claim 16 wherein the carrier is glass beads.

18. A method of preparing a human blood serum sample for vitamin $B_{12}$ competitive binding assay which comprises: treating the sample with a vitamin $B_{12}$ analogue, dithiothreitol at a concentration in the range of about 0.04 N to about 0.10 N and sodium hydroxide at a concentration in the range of about 0.3 N to about 1.0 N; and incubating said mixture under ambient conditions.

19. The method of claim 18 which, after incubation, comprises: neutralizing said mixture to a pH in range of about 4 to about 10; and adding to said mixture intrinsic factor bound to a solid inert carrier.

20. The method of claim 18 which further comprises: adding radioactive labelled vitamin $B_{12}$ to said sample.

21. The method of preparing a mammalian blood, tissue or serum sample for vitamin $B_{12}$ and/or folate assay which comprises treating the sample at ambient conditions with at least two materials to destroy and/or inhibit substantially all endogenous binding protein and substantially all IF-blocking antibodies.

22. The method of claim 21 in which the sample is also treated with a material to bind endogenous binding protein.

23. The method of claim 21 in which the sample undergoing preparation is treated with the two materials to destroy and/or inhibit endogenous binding protein and IF-blocking antibodies substantially simultaneously.

* * * * *

UNITED STATES PATENT AND TRADEMARK OFFICE
CERTIFICATE OF CORRECTION

PATENT NO. : 4,451,571
DATED : May 29, 1984
INVENTOR(S) : Robert H. Allen

It is certified that error appears in the above—identified patent and that said Letters Patent is hereby corrected as shown below:

Column 9, Line 56: "non-heating" should read --non-heated--

Column 10, Line 54: "betamencaptoethanol" should read --betamercaptoethanol--

Column 24: In TABLE IX, the first two lines in the table under the two far right columns (Standard % & Modified %) "-" should read -- -0.8--, and the "0.8"'s should be deleted Column 24: In TABLE IX, the fifteenth line of the table under the fifth column (Modified %) "-0.8" should be deleted. The -0.8 should be moved one column to the right (Standard %).

Column 34, Line 9: "out" should read --our--

Signed and Sealed this

Ninth Day of October 1984

[SEAL]

Attest:

*Attesting Officer*

GERALD J. MOSSINGHOFF

*Commissioner of Patents and Trademarks*